United States Patent
Green

(10) Patent No.: US 9,827,441 B2
(45) Date of Patent: Nov. 28, 2017

(54) PHOTOTHERMAL NANOSTRUCTURES IN TUMOR THERAPY

(71) Applicant: Hadiyah-Nicole Green, Atlanta, GA (US)

(72) Inventor: Hadiyah-Nicole Green, Atlanta, GA (US)

( * ) Notice: Subject to any disclaimer, the term of this patent is extended or adjusted under 35 U.S.C. 154(b) by 0 days.

(21) Appl. No.: 15/342,470

(22) Filed: Nov. 3, 2016

(65) Prior Publication Data

US 2017/0072216 A1 Mar. 16, 2017

Related U.S. Application Data

(63) Continuation of application No. 13/841,259, filed on Mar. 15, 2013.

(60) Provisional application No. 61/617,019, filed on Mar. 28, 2012.

(51) Int. Cl.
*A61B 6/00* (2006.01)
*A61N 5/06* (2006.01)
*B05D 3/10* (2006.01)

(52) U.S. Cl.
CPC ............ *A61N 5/062* (2013.01); *B05D 3/108* (2013.01); *A61N 2005/063* (2013.01); *A61N 2005/0644* (2013.01); *A61N 2005/0659* (2013.01)

(58) Field of Classification Search
CPC ............ A61N 5/062; A61N 2005/0659; A61N 2005/0644; A61N 2005/063; B05D 3/108
USPC .................................. 600/407–480
See application file for complete search history.

(56) References Cited

U.S. PATENT DOCUMENTS

| | | | |
|---|---|---|---|
| 5,361,764 A * | 11/1994 | Reynolds | G01R 33/34061 324/318 |
| 8,313,773 B2 | 11/2012 | Kim et al. | |
| 9,156,088 B2 | 10/2015 | Otsuka et al. | |
| 2003/0152517 A1* | 8/2003 | Peyman | A61K 41/0052 424/9.6 |
| 2004/0180369 A1 | 9/2004 | Franzen et al. | |
| 2007/0088206 A1* | 4/2007 | Peyman | A61B 5/14532 600/319 |

(Continued)

OTHER PUBLICATIONS

Niidome, Takuro et al., Poly(ethylene glycol)-modified gold nanorods as a photothermal nanodevice for hyperthermia, J. Biomater Sci Polym Ed. 2009; 20(9): 1203-15.

(Continued)

*Primary Examiner* — Sanjay Cattungal
(74) *Attorney, Agent, or Firm* — Fox Rothschild LLP

(57) ABSTRACT

Methods, structures, devices and systems are disclosed for implementing a photothermal therapy using nanostructures. In one aspect, a device to produce a photothermal effect includes a particle having a molecular layer functionalized onto the external surface of the particle and structured to attach to one or more targeting molecules capable of binding to a receptor site of a cell, in which the particle is configured to absorb light energy at a particular wavelength to produce a plasmon resonance effect that causes the particle to emit heat energy. In some implementations, the device is deployed in an organism having a tumor that includes a plurality of the cell and binds to the receptor site of the tumor by the targeting molecules, in which the light energy is emitted at a region of the organism that contains the tumor and the heat energy causes cellular death of the tumor cell.

6 Claims, 12 Drawing Sheets

(56) References Cited

U.S. PATENT DOCUMENTS

| | | |
|---|---|---|
| 2008/0131939 A1 | 6/2008 | Roper |
| 2009/0093551 A1 | 4/2009 | Bhatia et al. |
| 2011/0052671 A1 | 3/2011 | Zasadzinski et al. |
| 2011/0287035 A1* | 11/2011 | Peyman .............. A61K 41/0028 424/178.1 |
| 2011/0313298 A1* | 12/2011 | Rylander ............. A61B 5/0059 600/478 |
| 2012/0191148 A1 | 7/2012 | McKenna et al. |
| 2012/0226139 A1* | 9/2012 | Peyman .............. A61K 41/0028 600/411 |
| 2013/0338627 A1* | 12/2013 | Rylander .............. A61M 5/158 604/501 |
| 2014/0012224 A1 | 1/2014 | Zhang et al. |
| 2015/0209566 A1 | 7/2015 | Peyman |
| 2015/0265725 A1 | 9/2015 | Peyman |

OTHER PUBLICATIONS

Huang, Xiaohua et al., Cancer cell imaging and photothermal therapy in the near-infrared region by using gold nanorods, J Am Chem Soc. Feb. 15, 2006; 128(6): 2115-20.

Green, H.M. et al., A minimally invasive multifunctional nanoscale system for selective targeting, imaging, and NIR photothermal therapy of malignant tumors, Proc. SPIE7910, Reporters, Markers, Dyes, Nanoparticles, and Molecular Probes for Biomeidcal Applications III, 79100B (Feb. 7, 2011); doi:10.1117/12.875792.

\* cited by examiner

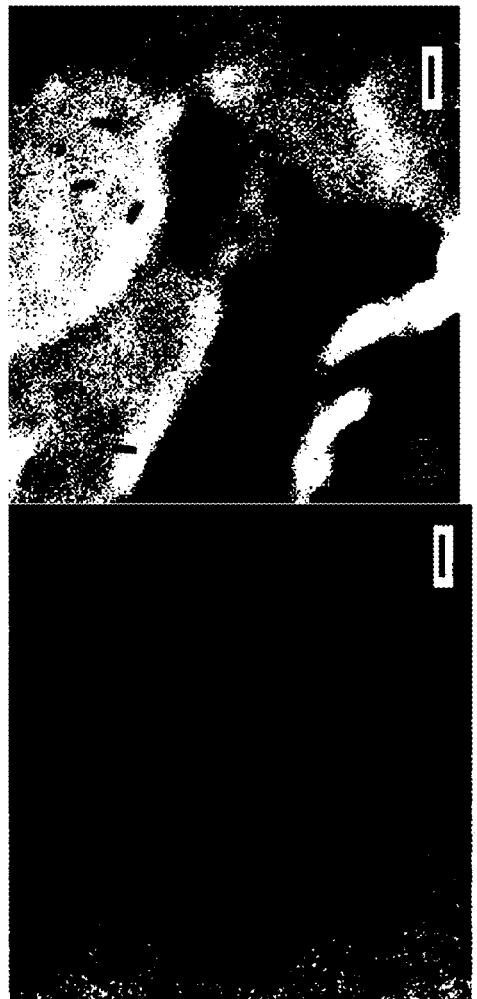
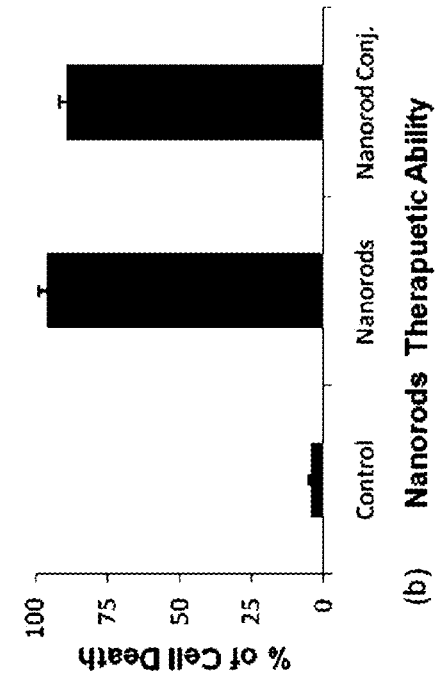
FIG. 2A  FIG. 2B  FIG. 2C
FIG. 4A
FIG. 4B

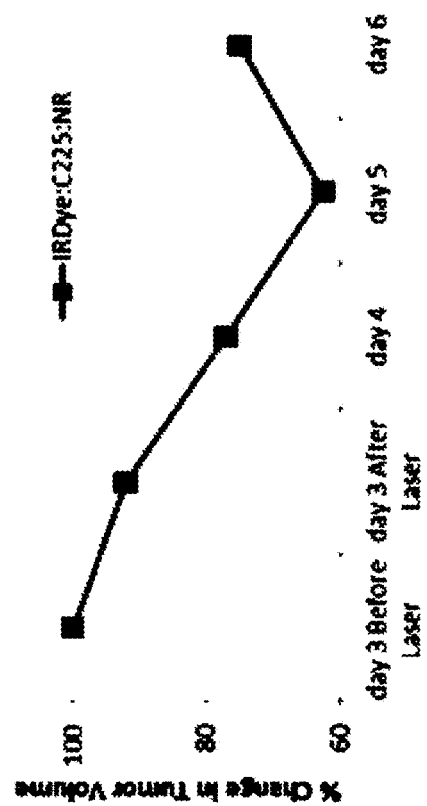
FIG. 11F
FIG. 11G
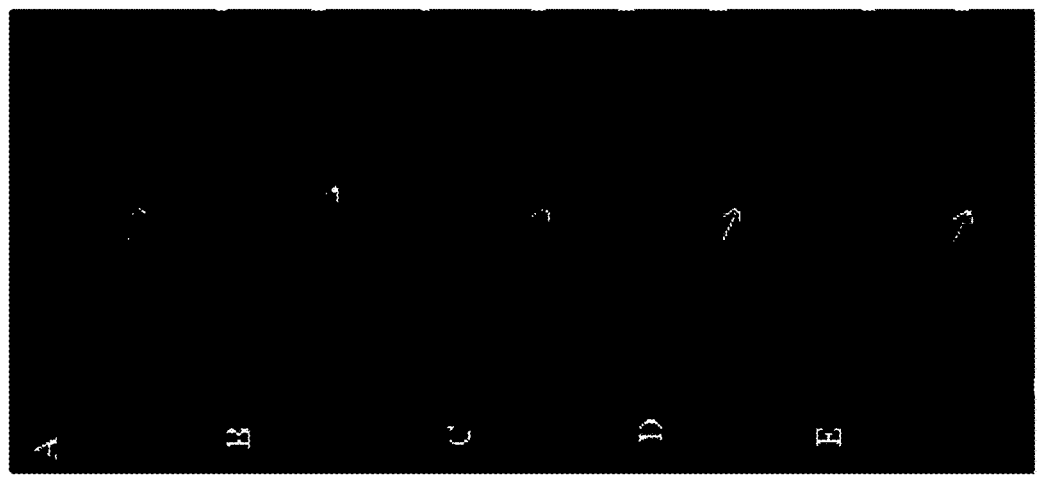
FIG. 11A
FIG. 11B
FIG. 11C
FIG. 11D
FIG. 11E

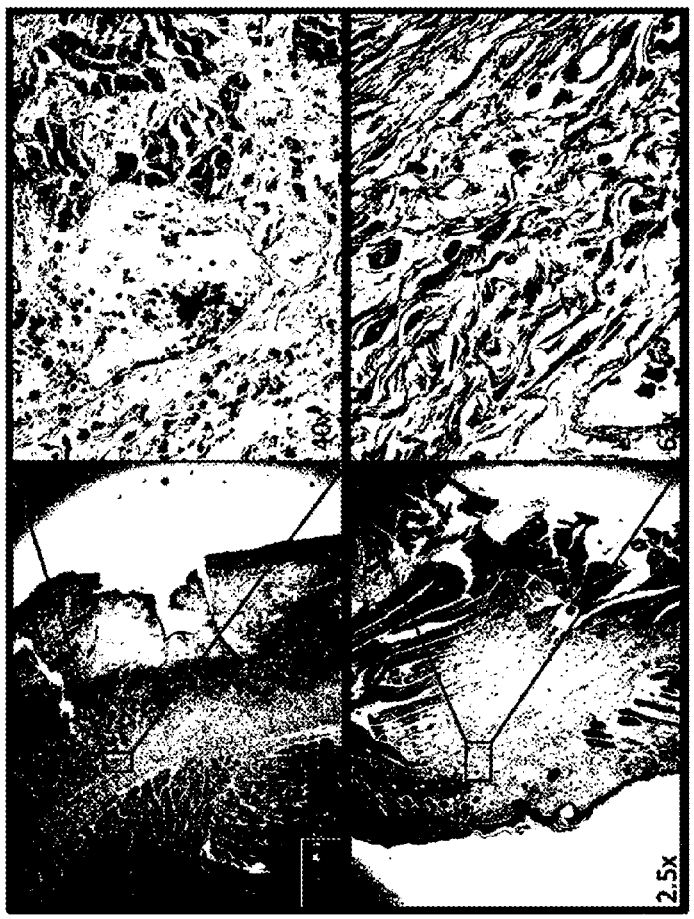
FIG. 16A
FIG. 16B
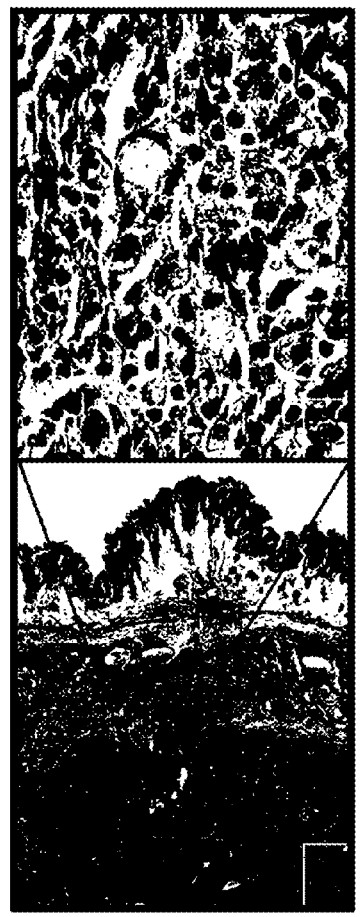
FIG. 17
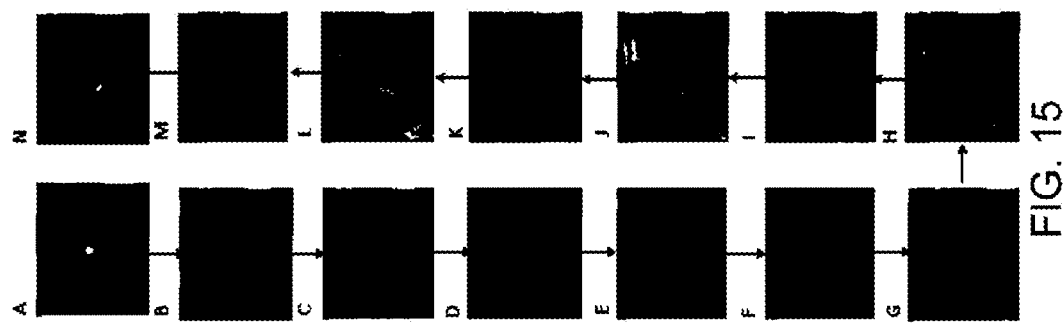
FIG. 15

PHOTOTHERMAL NANOSTRUCTURES IN TUMOR THERAPY

CROSS-REFERENCE TO RELATED APPLICATIONS

This patent document is a continuation of U.S. patent application Ser. No. 13/841,259, filed Mar. 15, 2013, which claims the priority of U.S. Provisional Application No. 61/617,019 entitled "PHOTOTHERMAL NANOSTRUCTURES IN TUMOR THERAPY" filed on Mar. 28, 2012. The entire disclosure of both applications are hereby incorporated by reference for all purposes.

STATEMENT REGARDING FEDERALLY SPONSORED RESEARCH OR DEVELOPMENT

This invention was made with government support under grant EPS-0814103 awarded by the National Science Foundation (NSF) and grant 1R21DE019232-01A2 awarded by the National Institutes of Health (NIH). The government has certain rights in the invention.

TECHNICAL FIELD

This patent document relates to systems, devices, and processes that use nanoscale technologies.

BACKGROUND

Nanotechnology provides techniques or processes for fabricating structures, devices, and systems with features at a molecular or atomic scale, e.g., structures in a range of one to hundreds of nanometers in some applications. For example, nano-scale devices can be configured to sizes similar to some large molecules, e.g., biomolecules such as enzymes. Nano-sized materials used to create a nanostructure, nanodevice, or a nanosystem that can exhibit various unique properties, e.g., including optical properties, that are not present in the same materials at larger dimensions and such unique properties can be exploited for a wide range of applications.

SUMMARY

Techniques, systems, devices, and materials are described for fabricating and implementing photothermal nanostructures in targeted tumor therapy.

In one aspect of the disclosed technology, a device for producing a photothermal effect includes a particle having a molecular layer functionalized onto the external surface of the particle and structured to attach to at least one targeting molecule capable of binding to a receptor site of a cell, in which the particle is configured to absorb light energy at a particular wavelength to produce a plasmon resonance effect that causes the particle to emit heat energy.

Implementations of the device can optionally include one or more of the following features. For example, the at least one targeting molecule of the device can be a tumor-targeting antibody, e.g., including an anti-epidermal growth factor receptor antibody. The device can be deployed in an organism having a tumor that includes a plurality of the cell and binds to the receptor site of the tumor by the targeting molecule, in which the light energy is emitted at a region of the organism that contains the tumor, and in which the heat energy causes cellular death of the tumor cell. For example, the particles can be deployed in the organism by direct injection into the tumor. In some implementations, the particle of the device can include a length dimension in the nanometer range. In some implementations, the particle of the device can be configured from a material that includes, but is not limited to, gold, silver, iron, carbon, or silicon. In some implementations, the particle of the device can be configured as a rod, sphere, cone, cage, cube, tube, or other geometry. In some implementations, the particle of the device can include an aspect ratio of 4:1. For example, the particular wavelength of the light energy can be in a near infrared range to produce the plasmon resonance effect. In some implementations, the molecular layer of the device can include polyethylene glycol (PEG). In some implementations, the at least one targeting molecule can be structured to attach a fluorophore.

In another aspect of the disclosed technology, a method to perform predictive calculations of a photothermal therapy includes determining at least one characteristic of a tissue in an organism, the characteristic of the tissue including a diameter, volume, shape, or depth beneath the outer surface of the organism; determining parameters of nanoparticles including a cross-section absorption value corresponding to a light energy absorption wavelength and at least one of shape, size, material, and aspect ratio, in which the nanoparticles are configured to attach to the tissue and undergo a plasmon resonance effect induced by light energy at the light energy absorption wavelength to emit heat energy; determining a temperature to induce within the tissue; and determining output parameters of a laser to emit light at wavelengths including the light energy absorption wavelength based at least in part upon the determined temperature and the determined parameters.

Implementations of the method can optionally include one or more of the following features. In some implementations, the method further includes determining a concentration of nanoparticles to deploy by direct injection into the tissue. In some implementations, the method further includes calculating output power of the laser based at least in part upon one of heat dissipation and conductivity values within the tissue or shape factor values of the tissue and/or determining time of exposure of the laser. For example, as part of the method, the light can be emitted at a region of the organism that contains the tissue and the attached nanoparticles, e.g., the tissue being a tumor. For example, as part of the method, the heat energy can cause cellular death of a plurality of cells of the tumor.

In another aspect, a method for producing photothermal nanorods includes fabricating nanorod structures, the nanorod structures configured to absorb light energy at a particular wavelength to produce a plasmon resonance effect that causes the particle to emit heat energy, coating the nanorod structures with a biocompatible molecular layer, and conjugating the biocompatible molecular layer-coated nanorod structures with a targeting ligand and an imaging agent to form functionalized photothermal nanorods, the conjugating including: determining a molar ratio of a cross-linking agent to the targeting ligand, adding the targeting ligand at a particular amount to a linker solution containing the cross-linking agent to form a ligand cross-linker solution, the linker solution having a particular concentration of the cross-linking agent to comply with the determined molar ratio, adding the imaging agent at a particular amount to the ligand cross-linker solution to form an imager ligand cross-linker solution, and reacting the biocompatible molecular layer-coated nanorod structures with the imager ligand cross-linker solution.

In another aspect, a photothermal nanostructure device includes a structure formed of a rod, sphere, cone, cage, cube, or tube having at least one dimension within the nanometer scale, the structure configured to absorb light energy at a particular wavelength to produce a plasmon resonance effect that causes the particle to emit heat energy, a biocompatible molecular layer formed on at least some of the exterior of the structure, and a molecular probe attached to the biocompatible molecular layer, the molecular probe including a targeting ligand conjugated to an imaging agent, the targeting ligand capable of binding to a receptor site of a cell, in which the molecular probe is formed by determining a molar ratio of a cross-linking agent to the targeting ligand, adding the targeting ligand at a particular amount to a linker solution containing the cross-linking agent to form a ligand cross-linker solution, the linker solution having a particular concentration of the cross-linking agent to comply with the determined molar ratio, and adding the imaging agent at a particular amount to the ligand cross-linker solution to form an molecular probe in solution.

In another aspect, a method to administer a photothermal therapy by direct injection of nanoparticles into a tissue includes injecting a photothermal nanoparticle device directly into a tumor in an organism, the photothermal nanoparticle device including a nanostructure having a molecular layer functionalized onto an external surface of the nanostructure, the nanostructure configured to absorb light energy at a particular wavelength to produce a plasmon resonance effect that causes the nanostructure to emit heat energy, and emitting the light energy at a region of the organism that contains the tumor, in which the heat energy causes cellular death of cells of the tumor.

In another aspect, a method to administer a photothermal therapy by direct injection of nanoparticles into a tissue includes injecting a photothermal nanoparticle device directly into a tumor in an organism, the nanostructure configured to absorb light energy at a particular wavelength to produce a plasmon resonance effect that causes the nanostructure to emit heat energy, and emitting the light energy at a region of the organism that contains the tumor, in which the heat energy causes cellular death of cells of the tumor.

The disclosed technology can be implemented to provide a near infrared (NIR) photothermal therapy as a localized, minimally invasive tumor regression therapy utilizing functionalized nanoparticles as a physical contrast agent and therapeutic agent. The subject matter described in this patent document can be implemented in specific ways that provide one or more of the following features. For example, an exemplary NIR laser irradiation, transparent to normal tissue, can be configured to overlap with plasmon resonance absorption of exemplary nanostructures, e.g., gold nanoparticles (AuNPs). The exemplary AuNPs can convert the absorbed NIR light energy into thermal energy and cause localized destruction of surrounding tissue. For example, techniques are disclosed for conjugating exemplary nanostructures to tumor-targeting ligands, e.g., including AuNPs conjugated to tumor-specific antibodies that can improve the targeting efficiency of AuNPs to malignant tumors. For example, targeting antibodies conjugated to the polyethylene glycol coated (PEGylated) gold nanorods (AuNRs) are disclosed. In some examples, the disclosed technology can be implemented in cancer types that over-express the epidermal growth factor receptor (EGFR). For example, exemplary implementations of the disclosed technology were demonstrated that included the anti-EGFR antibody labeled with a NIR fluorescent dye and conjugated to PEGylated AuNRs (dye-antibody-AuNR). Exemplary advantages of the disclosed technology include in vivo feasibility of a minimally invasive modality, e.g., which combines active targeting, fluorescent imaging, and NIR photothermal treatment of malignant tumors for a variety of cancer types, e.g., including, but not limited to, colorectal, ovarian, cervical, breast, pancreatic, bladder, skin and prostate cancers.

BRIEF DESCRIPTION OF THE DRAWINGS

FIGS. 2A-2C show transmission electron microscopy (TEM) images of exemplary functionalized nanorods.

FIGS. 4A and 4B show exemplary data plots demonstrating antibody binding ability and therapeutic ability of exemplary functionalized nanorods.

FIGS. 11A-11G show exemplary data of active targeting, fluorescence imaging and near infrared photothermal therapy of malignant tumors.

FIG. 15 shows exemplary photographic images of a tumor treated with an exemplary photothermal nanostructure therapy.

FIGS. 16A and 16B show histology images of a tumor directly injected with exemplary functionalized nanorods with laser treatment.

FIG. 17 shows histology images of a tumor.

DETAILED DESCRIPTION

Figure 1:
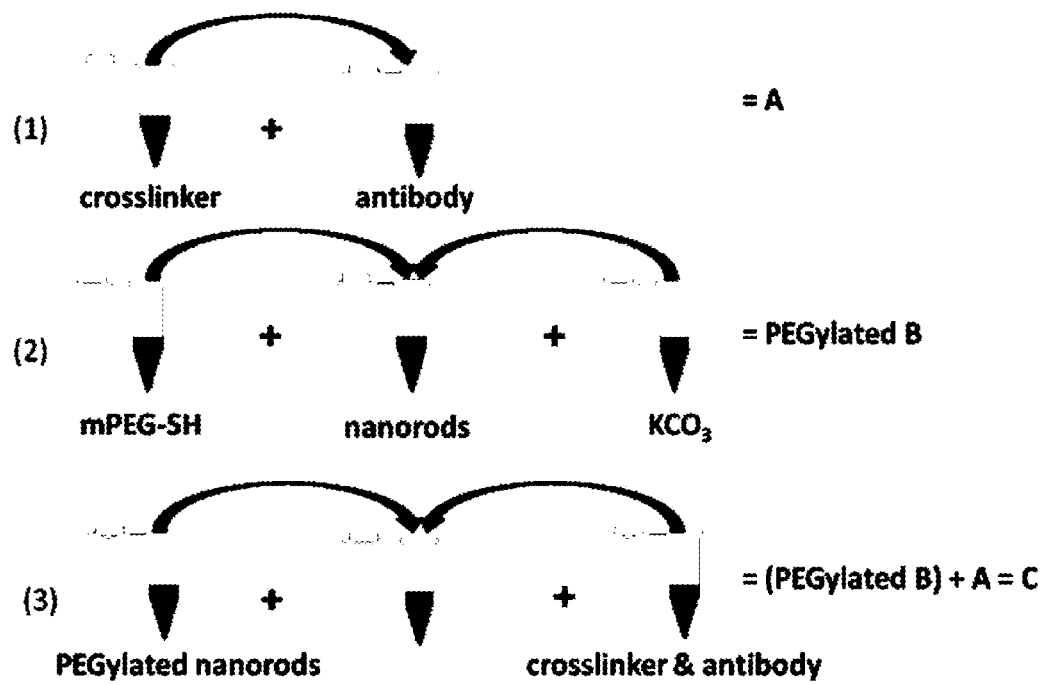
FIG. 1 shows an illustrative schematic of an exemplary nanorod functionalization protocol.

Techniques, systems, devices, and materials are described for fabricating and implementing photothermal nanostructures in targeted tumor therapy.

Active tumor targeting and subsequent tumor regression present challenges for cancer therapy. The medical and scientific communities have made significant advances to improve treatment options, yet cancer is still one of the leading causes of death globally. In cancer treatments, it is desirable to actively target and selectively treat only the malignant cells while leaving normal cells unharmed. Improvements to the existing standard of care are needed to combine early detection with targeted, selective, and repeatable treatment for loco-regional, recurring, and inoperable tumors.

In some aspects of the disclosed technology, a photothermal therapy (PTT) based on optical radiation in a suitable spectral range, e.g., the near infrared (NIR) range, can be implemented as a localized, minimally invasive therapy utilizing nanoparticles as a physical contrast agent and therapeutic agent. For example, the disclosed PTT techniques can utilize a physical contrast agent in an exemplary form of gold nanoparticles (AuNPs) having plasmon resonance in the NIR spectral range where normal tissue is transparent. The AuNPs convert the absorbed NIR light energy into thermal energy enabling cell death.

The therapeutic efficacy of the combination of AuNPs and NIR light has been demonstrated with nanospheres and nanorods in vitro and using the enhanced permeability and retention effect (EPR), dendrimers, and nanocarriers for passive and active tumor delivery in vivo. For example, conventional PTT techniques include limitations that exist in part because of a lack of effective protocols for systemic delivery of nanoparticles to tumors, a lack of quantitative approach for effective PTT with the use of direct injection of nanoparticles, compromised in vivo imaging capabilities, and a lack of a multifunctional system to target, image, and treat tumors.

The disclosed technology can be implemented to provide systems, devices, materials, and techniques that overcome various limitations of photothermal therapies, for example, by producing multifunctional conjugates (e.g., functionalized nanoparticles) for selective targeting, imaging, and laser-based (e.g., NIR) photothermal therapy. A quantitative approach can be used to achieve effective PTT by using direct injection of pre-calculated concentrations of nanoparticles and directing laser power to the injected nanoparticles. The disclosed multifunctional system can be implemented to achieve the advantage of imaging of fluorescently-labeled targeting ligands (e.g., tumor specific antibodies) conjugated to nanoparticles and photothermal-initiated necrosis of malignant cells due to localized heating of nanoparticles by continuous wave laser irradiation.

For example, the disclosed technology includes durable functionalization techniques that protect the conjugate bonds from being broken by the physiological conditions of the body, reduces non-specific binding, ensures active delivery of the nanoparticles to the malignant tumor site, and increases the efficacy of the NIR laser treatment. In this regard, an exemplary functionalization technique can include conjugating targeting antibodies to PEGylated AuNRs. For example, another exemplary functionalization technique can include attaching fluorescent label molecules to the functionalized AuNRs, e.g., conjugating fluorescent dyes to the tumor-targeted antibodies of the PEGylated AuNRs. For example, while gold nanoparticles in PTT served the dual role of therapeutic and contrast agents in vitro, their imaging capabilities in vivo can be limited. Therefore, by using fluorescently labeled tumor-targeted antibodies, imaging of tumors in real time can be dramatically improved. Excitation of the fluorescent IRDye can create a visual contrast between tumor and the surrounding non-tumor tissue. For example, after conjugation to gold nanorods (dye-antibody-nanorod), the fluorescently labeled tumor-targeted antibody (dye-antibody) functionalized AuNRs can actively be locally delivered to tumors and enabled real time imaging. Disclosed are exemplary dye-antibody-nanorod conjugates, delivered to tumors, and followed by treatment with NIR light, to reduce tumor cell viability in vitro and in vivo.

The exemplary targeting techniques can deliver functionalized nanostructures to target tumor cells and avoid uptake by non-target cells, tissues, and systems, e.g., such as the reticuloendothelial system in the liver, spleen, and kidney, which can otherwise prevent up to 90% of injected nanoparticles from reaching the tumor. The disclosed technology includes techniques and systems that optimize intravenous nanoparticle delivery to the tumor. In other examples, photothermal nanoparticles can be delivered to the target tumor by circumventing the targeted systemic delivery of the photothermal nanoparticles and directly injecting photothermal nanoparticles into the tumor. For example, disclosed are results of exemplary implementations showing tumor reduction effects from an exemplary combination of one-time 10-minute NIR laser treatment and an intratumoral injection of gold nanorods. In other examples, disclosed are results of other variations of intratumoral injections of nanorods as well as active tumor targeting, fluorescence imaging, and near infrared photothermal therapy. These disclosed techniques can be implemented for combining early detection with targeted, selective, and repeatable treatment for a variety of squamous cell carcinomas that over-express the epidermal growth factor receptor (EGFR) including, for example, but not limited to, head and neck, lung, colorectal, ovarian, cervical, breast, bladder, pancreatic, and prostate cancers.

Examples of the disclosed techniques are described for conjugating gold nanoparticles to tumor-specific antibodies, e.g., including fabrication of polyethylene glycol coated (PEGylated) gold nanorods (GNRs) and conjugation of the PEGylated GNRs to an anti-EGFR antibody. Exemplary characterizations of the conjugation efficiency of the GNRs are disclosed, e.g., by comparing the efficiency of antibody binding and the photothermal effect of the GNRs before and after conjugation. Exemplary implementations of near infrared photothermal therapy (NIRPTT) using the exemplary anti-EGFR antibody-PEGylated GNRs were performed. Exemplary characterizations of the efficacy of NIRPTT using the functionalized nanostructures of the disclosed technology are disclosed, e.g., by comparing NIRPTT with GNRs alone and NIRPTT using anti-EGFR antibody-PEGylated GNRs.

For example, a durable conjugation process is needed to protect the conjugation from the physiological conditions of the body, reduce non-specific binding, ensure active delivery of the nanoparticles to the malignant tumor site and increase the efficacy of the NIR laser treatment. Incorporating the disclosed methods of active targeting can improve the impact of PTT, e.g., making it a viable approach for a variety of carcinomas that over-express particular biomolecules, such as the epidermal growth factor in head and neck, colorectal, ovarian, skin, cervical, breast, bladder, pancreatic, and prostate cancers. Described are techniques to produce nanostructures capable of active targeting of tumors, e.g., AuNPs-to-antibody conjugation using covalent bonds to ensure specific delivery to the tumor.

Exemplary materials and methods are described. For example, Cetuximab (ImClone Systems, New York, N.Y.), a recombinant human/mouse chimeric monoclonal IgG antibody, was used in exemplary implementations. This monoclonal antibody binds specifically to the extracellular domain of the human EGFR which is over-expressed in head and neck cancers. Cetuximab is composed of the Fc regions of a murine anti-EGFR antibody and human immunoglobulin IgG1 heavy and kappa light chain constant regions and has an approximate molecular weight of 152 kDa. Cetuximab is supplied as a 2 mg/mL solution containing sodium chloride, sodium phosphate dibasic heptahydrate, sodium phosphate monobasic monohydrate, in water and has a pH ranging from 7.0 to 7.4.

For example, Long Chain Succinimidyl 6-(3-[2-pyridyldithio]-propionamido) hexanoate (LC-SPDP), MW=425.52 g/mol, Spacer Arm Length=15.6 Angstroms (Thermo Scientific, Rockford, Ill.), was employed to bioconjugate Cetuximab to gold nanorods. LC-SPDP is a heterobifunctional, thiol-cleavable and membrane permeable crosslinker. LC-SPDP contains an amine-reactive N-hydroxysuccinimide (NHS) ester that will react with lysine residues to form a stable amide bond on the surface of the antibody. The other end of the spacer arm is terminated in the pyridyl disulfide group that will react with sulfhydryls to form a reversible disulfide bond that reacts with thiol PEGylated gold nanorods.

Exemplary gold nanorods were fabricated based on procedures as described here. Stock Solutions Preparation: 30 mL of HPLC grade water was placed on ice. While the temperature of the water was cooling to 0 degrees, the other solutions were prepared: 1 mM Gold (III) chloride trihydrate, $(HAuCl_4 \cdot 3H_2O)$ (Sigma-Aldrich, St. Louis, Mo.), 200 mM cetyltrimethylammonium bromide (CTAB) (Sigma-Aldrich, St. Louis, Mo.), 78.8 mM Ascorbic acid, and 32 mM $AgNO_3$ (Sigma-Aldrich, St. Louis, Mo.). A hot-water bath, less than 50° C., was used to dissolve CTAB. Ice-cold water was rapidly added to the $NaBH_4$ and the solution was returned to ice since $NaBH_4$ solution is unstable and rapidly decomposes at room temperature. Seeds Solution Preparation: 2.5 mL of 1 mM of $HAuCl_4 \cdot 3H_2O$; 5 mL 200 mM CTAB; and 0.6 mL ice-cold 10 mM $NaBH_4$, were mixed and incubated at room temperature (25° C.) for 2 hours before use. This last step is needed to disintegrate the remaining $NaBH_4$ to prevent unwanted seeds appearing in the growth solution. The seed solution at this stage should be beige-brown in color. Growth Solution Preparation: 20 mL of 1 mM $HAuCl_4 \cdot 3H_2O$ and 20 mL of 200 mM CTAB were combined with 804, of 32 mM $AgNO_3$, 280 µL of 78.8 mM Ascorbic acid, and 64 µL of seed solution. The solution color changed from yellow-orange to colorless and then finally to deep pink. Nanorods were allowed to grow undisturbed for 2 h at room temperature. The $NaBH_4$ should completely decompose during this stage.

Exemplary gold nanorods were functionalized based on procedures as described here. Gold nanorod biofunctionalization using polyethylene glycol (PEG): Gold nanorods were fabricated with the surfactant, CTAB, as a capping agent to control the size of the nanorod. The process of using poly-ethylene glycol (PEG) to replace the CTAB on the surface of nanorods is known as 'PEGylation' whereby the nanorods are 'PEGylated.' PEGylation can be advantageous because it increases biocompatibility and stability, decreases immunogenicity and adsorption to the negatively charged luminal surface of blood vessels, and suppresses the non-specific binding of charged molecules. During the CTAB removal process, the nanorods were centrifuged at (7000 g, 20 mM), decanted, and the pellet was resuspended in 2 mL of 100 mM PBS-EDTA. The nanorods were then biofunctionalized, PEGylated, using 1 mM of thiol-terminated methoxy-poly-ethylene glycol (mPEG-SH) (MW=5000, Nanocs, New York, N.Y.) and 2 mM of Potassium Carbonate (Acros, Fair Lawn, N.J.) and incubated overnight. A covalent bond was formed between the thiol group of PEG and the surface of the gold nanorod replacing the CTAB. A VersaMax microplate reader was used to determine the relative optical density and concentration of the nanorods. The measured concentration of the PEGylated nanorods was $CONC_{PEG-NR}$=4.41 mg/mL. The optical density of the PEGylated nanorods was $OD_{PEG-NR}$=8.24 (~$1.50 \times 10^{11}$ GNRs/mL) unless otherwise noted. UV-VIS Spectrophotometer was used to calculated the average peak of the absorption spectra as $\lambda$=784 nm. Imaging by Transmission Electron Microscopy (TEM) was used to verify consistency in shape and size.

Gold nanorod conjugation to antibody followed by PEGylation: Bioconjugation of gold nanorods to antibodies was carried out with the LC-SPDP following the exemplary procedure provided. For example, after equilibrating the vial of LC-SPDP reagent to room temperature, 20 mM LC-SPDP was prepared in dimethylsulfoxide, DMSO (Sigma-Aldrich, St. Louis, Mo.). For example, Cetuximab was used without modification. Twenty-five milliliters of LC-SPDP solution was added to 1 mL of Cetuximab solution and allowed to incubate for 60 min at room temperature yielding a calculated linker:antibody molar ratio of 37:1. The Cetuximab mixture was exchanged into 1 mL of pure PBS-EDTA buffer by using a Zeba desalt spin column (Pierce Biotechnology, Rockford, Ill.) or a Microcon centrifugal filter device (Millipore, Bedford, Mass.). Reaction byproducts, excess Cetuximab, and excess LC-SPDP were also removed by the desalting column. Forty milliliters of raw nanorods were centrifuged (7000 g, 20 min), decanted, and then resuspended in 1 mL of PBS-EDTA. Two and a half microliters of the antibody/cross-linker mix were added to the nanorod solution and then incubated at room temperature overnight. The nanorods were then PEGylated by adding 10 µL of 1 mM mPEG-SH and 100 µL of 2 mM potassium carbonate at room temperature and again incubated overnight. Finally, the bioconjugated nanorods were centrifuged, decanted, and resuspended in PBS-EDTA several times to remove excess CTAB and unreacted mPEG-SH.

Antibody conjugation to PEGylated gold nanorods: PEGylated gold nanorods were conjugated to an exemplary antibody, e.g., Cetuximab, by combining Cetuximab and the LC-SPDP crosslinker in varying molar ratios, desalted, and then added to nanorods that were previously PEGylated. Instead of PEGylating the conjugated nanorod-crosslinked-antibody unit, the already biocompatible PEGylated nanorod was crosslinked to the antibody. In the exemplary protocol, bioconjugation of gold nanorods to antibodies was carried out with the following modifications. Forty milliliters of raw nanorods were centrifuged (7000 g, 20 min), decanted, and then resuspended in 1 mL of PBS-EDTA. The nanorods were then PEGylated by adding 10 µL of 1 mM mPEG-SH and 100 µL of 2 mM potassium carbonate and incubated overnight. The biofunctionalized nanorods were centrifuged, decanted, and resuspended in PBS-EDTA several times to remove excess CTAB and mPEG-SH. Various amounts of the 20 mM crosslinker, LC-SPDP, in DMSO solution was added to 1 mL of Cetuximab and allowed to incubate for 60 min at room temperature yielding a tunable linker:antibody molar ratio. 100-200 µL of the antibody/cross-linker mix was added to the PEGylated nanorods and then incubated at room temperature overnight. Either a Zeba desalt spin column (Pierce Biotechnology, Rockford, Ill.) or a Microcon centrifugal filter device (Millipore, Bedford, Mass.) was used to exchange the buffer for PBS-EDTA and to remove the reaction byproducts of the PEGylated nanorod-antibody complex.

FIG. 1 shows an illustrative schematic of an exemplary nanorod conjugation protocol, e.g., including conjugation of antibody to PEGylated nanorod. As shown in FIG. 1, step 1 demonstrates attaching the crosslinker to the antibody, step 2 demonstrates PEGylating the nanorod, and step 3 demonstrates conjugating the antibody to the PEGylated nanorod. In this example, nanorods are functionalized with PEG, and not the nanorod-antibody conjugate.

Exemplary implementations were performed to characterize the exemplary functionalized gold nanorods, e.g., PEGylated AuNRs conjugated with at least one antibody and/or a fluorophore. For example, gold nanorod/antibody conjugations were examined for structure, consistency, and efficiency by TEM. Specifically, exemplary implementations used carbon only copper grids, uranyl acetate stain, and a FEI TecnaiT12 80 kv or 120 kv (Twin TEM, Hillsboro, Oreg.). Digital images were captured of the gold nanorods and conjugates on an AMT (Danvers, Mass.) 2 k camera. UV-VIS Spectrophotometer was used to measure percent transmittance and calculate the plasmon resonance absorption. A modified ELISA assay was used to evaluate the efficiency of antibody binding before and after conjugation to GNRs. 500 µL PBS was added to Recombinant Human epidermal growth factor receptor (EGFR)/ErbB1 Fc Chimera, CF (50 µg/vial R&D Systems, Inc., Minneapolis, Minn.) for a final concentration of 0.1 mg/mL and used 50 ng/100 µL of r EGF R in PBS w/Ca++ and Mg to coat a 96 well plate. The plate was covered with saran wrap or plate sealer and incubated overnight at 4° C. The plate was blocked with 1% BSA in PBS w/o CA++ and Mg for non-specific binding and incubated for 1 hr RT or stored at 4 degrees until use. The BSA or PBS was removed from wells and the samples were added, incubated for 1 hr, and washed with PBS several times. Samples were analyzed by the Pearl Impulse Imager (LI-COR, Lincoln, NB).

Exemplary implementations were performed for near infrared photothermal therapy using the exemplary functionalized gold nanorods, e.g., PEGylated AuNRs conjugated with at least one antibody and/or a fluorophore. For example, head and neck human squamous cell carcinoma (e.g., cell line SCC-5) was used in exemplary implementations. The HNSCC line was maintained in Dulbecco's Modified Eagle Medium (DMEM) containing 10% fetal bovine serum, supplemented with L-glutamine, penicillin, and streptomycin and incubated at 37° C. in 5% $CO_2$. The measured concentration of the PEGylated nanorods was $CONC_{PEG-NR}$=4.41 mg/mL. The optical density of the PEGylated nanorods is $OD_{PEG-NR}$=8.24 (~$1.50 \times 10^{11}$ particles/mL). Both PEGylated nanorods and nanorod-antibody conjugates were used with average plasmon resonance absorption of 785 nm. A NIR diode laser (SDL, Inc, San Jose, Calif., 8350) was used to perform the photothermal therapy of cells, 4 min exposure time, 785 nm wavelength, 9.5 $W/cm^2$ fluence. Cell viability assay was performed with 1:1 dilution of Trypan Blue.

The exemplary protocol demonstrated an enhancement in the targeted treatment of malignant tumors by improving the conjugation efficiency of GNRs to tumor targeted antibodies. For example, improved delivery of the nanorods was shown to make the NIR PTT more effective. The exemplary conjugation protocol can include the use of covalent bonds, sulfhydryl and amide group chemistry to improve conjugation efficiency. The order of conjugation and PEGylation were examined, as well as its effects on the nanorods forming clusters, aggregating, and the percentage of binding efficiency of the antibody. The binding efficiency of the antibody before and after conjugation was examined, as well as the therapeutic effect of the nanorods for photothermal therapy before and after conjugation.

Exemplary implementations were performed to identify a successful modality to selectively target gold nanorods to malignant cells by optimizing conjugation parameters to the anti-EGFR antibody, e.g., Cetuximab. For example, by conjugating nanorods with antibodies, the specificity of nanorods can be improved. The quality of the conjugation of nanorods to antibodies using the LC-SPDP crosslinker and PEG-SH can be affected by the sequential order of the steps as depicted in FIGS. 2A-2C.

The TEM images in FIGS. 2A-2C show the physical differences that the order of PEGylation and conjugation, as illustrated in FIG. 1, has on a collection of gold nanorods. The results obtained by implementing the disclosed methods using exemplary anti-EGFR antibody are shown in FIG. 2A. In conducted tests, the conjugated GNRs-antibody unit was PEGylated; this procedure resulted in more than a 70% loss of nanorod individuality, described here as aggregation.

FIGS. 2A-2C show exemplary TEM images of nanorod conjugation to antibody before PEGylation vs. PEGylated nanorod conjugation to antibody. FIG. 2A shows exemplary nanorods first conjugated to anti-EGFR antibody then PEGylated; FIG. 2B shows exemplary nanorods first PEGylated then conjugated to anti-EGFR antibody; and FIG. 2C shows exemplary PEGylated nanorods without antibody or crosslinker present. The exemplary scale bars shown in FIGS. 2A, 2B, and 2C represent 100 nm.

To overcome this aggregation, PEGylated GNRs were conjugated to antibodies, shown in FIG. 2B. More than 70% of the GNRs were observed in clusters of various shapes and sizes. In FIG. 2C, PEGylated GNRs are shown with no antibodies or crosslinker, as a control. Aggregation like in FIG. 2A or clustering like in FIG. 2B was not found using the same concentration of GNRs. This indicates that the nanorod-antibody interaction is affected by the order of conjugation and PEGylation.

Figure 3:
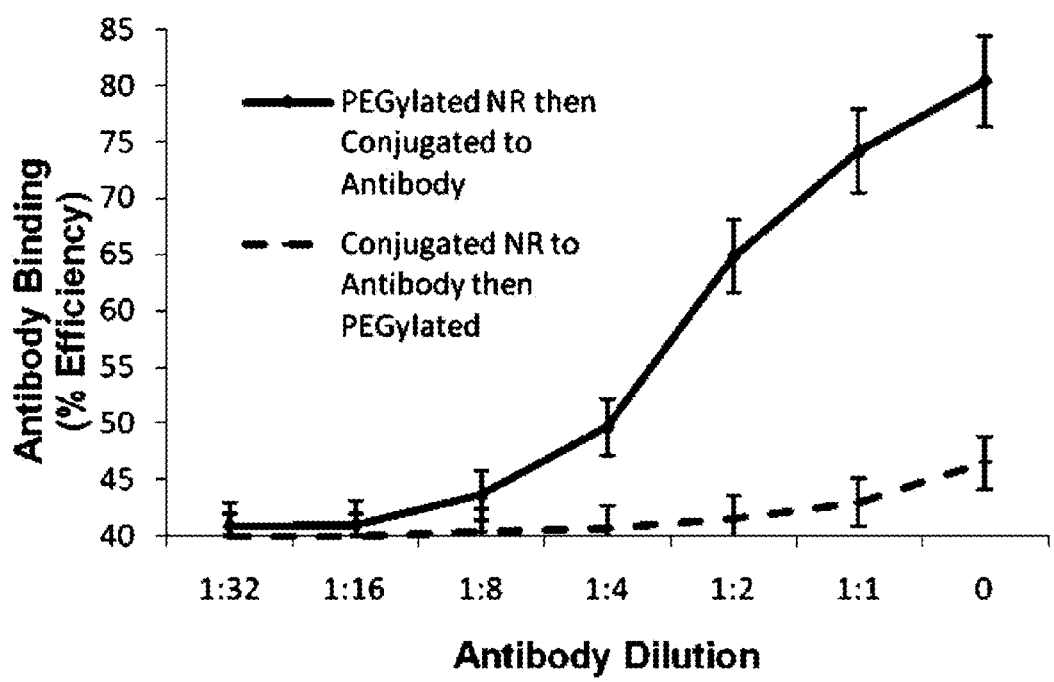
FIG. 3 shows exemplary data plot of an antibody binding assay.

Antibody binding efficiency was also affected by the PEGylation and conjugation order. Using the unconjugated antibody as the binding efficiency standard, the binding efficiencies was surveyed resulting from the protocols illustrated in FIG. 1 using a modified ELISA assay. In FIG. 3, a summary of the results for a titration of antibody concentrations and without any dilution to the antibody concentration is shown.

FIG. 3 shows exemplary data demonstrating a comparative antibody binding assay based on the sequential order of conjugation and PEGylation, summarizing the binding efficiency of antibodies when conjugated to nanorods then PEGylated (solid line) and antibodies conjugated to PEGylated nanorods (dashed line).

For example, increase in the antibody binding efficiency was observed as antibody concentration increases in both cases. For example, without any dilution to the antibody concentration, a 6.5% binding efficiency was measured for the antibodies conjugated to GNRs then PEGylated versus a 40.4% binding efficiency measured for the antibodies conjugated to the PEGylated GNRs. By modifying the order of conjugation and PEGylation, a 6-fold improvement was demonstrated in the binding efficiency of the conjugated antibody.

Exemplary parameters of photothermal therapy were optimized, e.g., without compromising the aspects of the disclosed technology already shown effective, for example, such as the targeting ability of the antibodies and the therapeutic ability of the nanorods when used in combination with the NIR laser. For example, the binding ability was measured of unconjugated anti-EFGR antibody to the antigen, e.g., the epidermal growth factor receptor. Using the unconjugated antibody as the standard of binding efficiency on a scale from 0 to 5, the binding efficiency of the antibody after being conjugated to PEGylated nanorods was demonstrated, as shown in FIG. 4A.

FIG. 4A shows exemplary data demonstrating an anti-EGFR antibody binding assay shows the antibody function before and after conjugation to the PEGylated gold nanorod. FIG. 4B shows exemplary data demonstrating a cell viability assay summarizes the percentage of cells dead after photothermal therapy with laser only, laser plus PEGylated nanorods, and laser plus nanorods conjugated to the anti-EGFR antibody.

For example, the binding efficiency was found to be slightly improved after conjugation from 3.93 to 4.4 on a scale from 0 to 5, e.g., but considering the standard error, the binding efficiency can be estimated to be approximately the same for the antibody before and after conjugation to PEGylated nanorods, FIG. 4A. This exemplary binding assay can confirm that the antibody is still binding after conjugation. The exemplary 9% difference in binding efficiency of antibody before and after conjugation to nanorods is relatively negligible when compared to the binding efficiency of the antibody that was conjugated to the nanorod then PEGylated which had a binding efficiency of 0.29, e.g., an 82% difference from the antibody binding before conjugation.

For example, GNR-mediated NIR PTT can provide approximately a 95% death rate, which is comparable to the results of the exemplary implementations performed from before and after conjugation. For example, in the process of optimizing the active targeting component by conjugating the GNRs to antibodies, the therapeutic capability was maintained. FIG. 4B shows the effect that conjugating the nanorods to antibodies has on photothermal therapy. The exemplary cell viability assay shows the percentage of dead cells after treatment as performed in vitro without washing cells after adding GNRs. For example, the cells were treated with the NIR laser only as a control, with the laser and PEGylated nanorods, and with the laser plus PEGylated nanorods conjugated to the anti-EGFR antibody. The percentages of dead cells after these treatments were 4.5%, 96%, and 89% respectively. There is only a 7% difference in the therapeutic effect for nanorods before and after the conjugation process which likely attributed to distance between to GNRs and the cell surface due to the antibody and crosslinker. The exemplary experiments were performed with a 785 nm diode laser at 9.5 W/cm$^2$, ~4 minutes using GNRs with $OD_{PEG-NR}$=4.12 (~8.65×10$^{11}$ particles/mL) and 300:1 crosslinker:antibody ratio.

Figure 5:
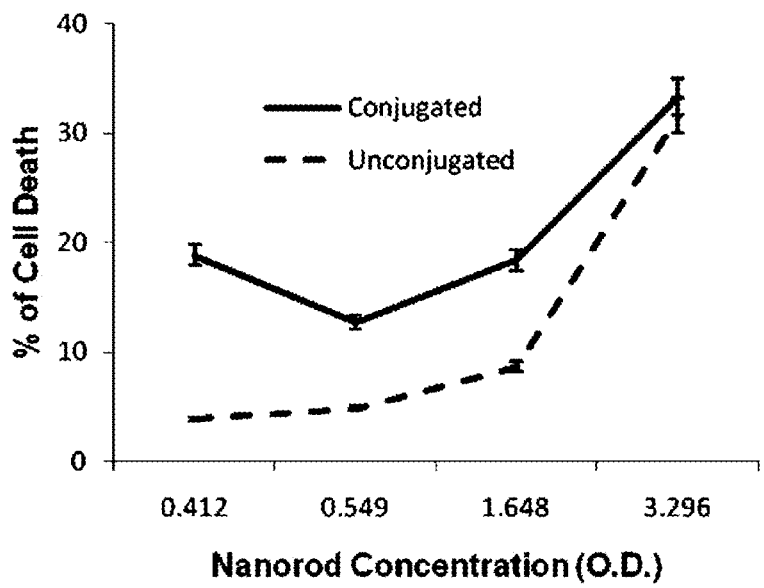
FIG. 5 shows an exemplary data plot of a cell viability assay.

The physiological conditions inside the body require a resilient and functional conjugation to ensure optimal delivery of the GNRs to malignant tumors and successful treatment upon arrival. Results of the exemplary implementations of the disclosed technology have shown that after conjugation, both the antibody binding efficiency and the GNRs therapeutic ability are individually comparable to their performance before conjugation. To further evaluate the conjugation performance and the photothermal effect with GNRs, cells were treated with GNRs, alone and conjugated, and washed with medium three times to remove any unbound GNRs. Exemplary results showed that there is some adsorption effect happening with the GNRs on the surface but this is distinguishable at very dilute concentrations of the GNRs. In FIG. 5, the percentage of cell death after NIR PTT was compared with GNRs alone and conjugated.

FIG. 5 shows exemplary data demonstrating a cell viability assay that shows the percentage of cell death of conjugated (solid line) and unconjugated (dashed line) nanorods after photothermal therapy with increasing nanorod concentration after three washes.

GNRs with optical densities of 0.412, 0.549, 1.648, and 3.296 were conjugated to antibody concentrations of 14.3, 19.1, 11.12 and 9.52 µg/mL, respectively. The exemplary results show a trend that as the nanorod concentration increases, the cell death increases. The difference in the percentage of cell death caused by NIR PTT is observed for lower concentrations of GNRs correlating to higher antibody concentrations. There may also a difference in the binding effects observed for the anti-EGFR antibody binding to the EGFR used in the assay as displayed in FIG. 3 and the binding that results from the EGFR expressed on the surface of the SCC-5 cells used for the cell viability experiment after three washes in FIG. 5. The antibody-to-nanorod ratio and resultant relative therapeutic effects and stoichiometry may also be included in the protocols of the disclosed technology.

Conducted tests and results demonstrated the efficacy of the disclosed technology, e.g., including optimizing the parameters for using covalent bonds to conjugate GNRs to the anti-EGFR antibody, Cetuximab. For example, the covalent conjugation of the antibody to GNR facilitates active targeting of the nanorods to the tumor site. This kind of active targeting was shown to be efficient, e.g., more efficient than PEGylation to an existing antibody-nanorod conjugate. Exemplary implementations characterized the efficiency of the conjugation of the gold nanorods to Cetuximab by comparing the antibody binding efficiency and the photothermal effect of nanorods before and after conjugation. For example, the percentage of antibody binding efficiency was shown 6 fold (33.9%) greater when conjugating the antibody to an already PEGylated nanorod versus PEGylating the nanorod-antibody conjugation. Exemplary implementations show that binding ability of the conjugated antibody to the epidermal growth factor receptor (EGFR) has not been affected by conjugation, whereas the binding efficiency was 3.93 before conjugation and 4.4 after conjugation on a scale from 0 to 5.

In addition, cell death by NIR photothermal therapy with the use of gold nanorods is not compromised following conjugation of gold nanorods to an antibody. The percentage of cells living after photothermal treatment with the laser and PEGylated nanorods was only 4%, when compared to the 11% of cells living after treatment with laser plus nanorods conjugated to the anti-EGFR antibody. The difference in the photothermal therapeutic effect for nanorods before and after the conjugation process is only a 7%. NIR photothermal treatment with the antibody-nanorod conjugate selectively heated the GNR and was sufficient to kill nearly 90% of tumor cells which is comparable to photothermal therapy with the GNR alone. These exemplary results indicate that nanorod-antibody conjugates can be implemented to improve active targeting agent in in vitro and in vivo applications. For example, the exemplary results described have shown active targeting and subsequent photothermal treatment of malignant cells, which can be implemented as a viable approach for the treatment of a variety of cancer types that over-express the epidermal growth factor including head and neck, colorectal, ovarian, cervical, skin, breast, bladder, pancreatic, and prostate cancers.

In another aspect of the disclosed technology, systems, devices, materials, and techniques are described for a minimally invasive active targeting, fluorescent imaging, and NIR photothermal treatment of malignant tumors, e.g., which can be applied to a variety of cancer types that over-express the epidermal growth factor receptor (EGFR).

A device for producing a photothermal effect includes a particle having a molecular layer functionalized onto the external surface of the particle and structured to attach to at least one targeting molecule capable of binding to a receptor site of a cell, in which the particle is configured to absorb light energy at a particular wavelength to produce a plasmon resonance effect that causes the particle to emit heat energy. In some implementations, the device can be configured as a gold nanorod. For example, a near infrared (NIR) laser (785 nm, ~9.5 W/cm$^2$, 10 minutes exposure) can be used to take advantage of the plasmon resonance absorption peak of exemplary device (e.g., gold nanorods (AuNRs)), e.g., of a ~785 nm peak absorption wavelength and aspect ratio of ~4. Exemplary targeting ligands and fluorescent molecules can be conjugated to the exemplary AuNR device to render the device multifunctional. For example, an anti-EGFR antibody, which targets the over-expressed EGFR on malignant cells, can be labeled with a NIR fluorescent dye and conjugated to PEGylated AuNRs (dye-antibody-AuNR). Techniques are described for determining the optimal molar ratio and conjugation of dye-antibody-AuNR that can facilitate the targeted delivery of the AuNR device to the tumor site. For example, the exemplary techniques can be implemented such that the conjugation does not affect the binding affinity of the antibody to the EGFR, the fluorescence of the IRDye, or the therapeutic qualities of the AuNRs. Exemplary implementations were performed showing exemplary NIR photothermal treatments using the AuNR device, e.g., with the dye-antibody-nanorod conjugate, which sufficiently killed approximately 90% of tumor cells in vitro and provided a substantial reduction in tumor size in vivo.

The AuNR devices can also be implemented to provide the ability to image in real-time with the active targeting and photothermal treatment of tissues, e.g., malignant tumors. For example, fluorescently-labeled tumor-targeted antibodies can be used for imaging of tumors in real time. Excitation of an exemplary fluorescent IRDye, e.g., attached to the AuNR device, can create a visual contrast between tumor and the surrounding non-tumor tissue. The exemplary fluorescently-labeled tumor-targeted antibody (dye-antibody), e.g., after conjugation to gold nanorods (dye-antibody-nanorod), can actively deliver the functionalized AuNRs to tumors and enable real time imaging. By optimizing the conjugation of gold nanorods to NIR fluorescently labeled antibodies and exciting with a near infrared laser, the in vivo efficacy of nanorods can be improved. Exemplary implementations were performed using the exemplary dye-antibody-AuNR conjugate devices (e.g., aspect ratio ~4, plasmon resonance peak ~785 nm) with NIR light which sufficiently reduced tumor cell viability in vitro and reduced tumor size in vivo.

A method of fabricating photothermal nanorod devices includes a process to fabricate photothermal nanorod structures, a process to coat the photothermal nanorod structures with a biocompatible molecular layer, and a process to conjugate biocompatible molecular layer-coated photothermal nanorod structures with at least one of a targeting ligand and/or imaging agent (e.g., fluorescent dye) using an engineered linking chemistry, described herein.

In some implementations of the process to conjugate the targeting ligand and/or imaging agent to the biocompatible molecular layer-coated nanorod structures, 20 mM of a cross-linker, LC-SPDP, in DMSO solution can be added to an antibody and allowed to incubate for 1 hour at room temperature yielding a tunable linker:antibody molar ratio. In some examples, the cross-linker:antibody molar ratio of 300:1 was implemented in the process. 2-20 μL of the fluorescent dye can be added to the antibody/cross-linker mix (e.g., 50-300 μL) formed in the prior step of the process. The formed fluorescently-labeled antibody can be added to the biocompatible molecular layer-coated nanorod structures (e.g., PEGylated nanorods) and then incubated at room temperature overnight. In some examples of the process, a Zeba desalt spin column (e.g., obtained from Pierce Biotechnology, Rockford, Ill.) or a Microcon centrifugal filter device (e.g., obtained from Millipore, Bedford, Mass.) can be used to exchange the buffer from PBS and to remove the reaction byproducts of the PEGylated nanorod-antibody complex.

Further details including exemplary materials and processing steps of the method are described. For example, Cetuximab (ImClone Systems, New York, N.Y.), a recombinant human/mouse chimeric monoclonal IgG antibody, binds specifically to the extracellular domain of the human EGFR which is over-expressed in head and neck squamous cell carcinomas (HNSCC). Cetuximab is composed of the Fc regions of a murine anti-EGFR antibody and human immunoglobulin IgG1 heavy and kappa light chain constant regions and has an approximate molecular weight of 152 kDa. Cetuximab is supplied as a 2 mg/mL solution containing sodium chloride, sodium phosphate dibasic heptahydrate, sodium phosphate monobasic monohydrate, in water and has a pH ranging from 7.0 to 7.4. IRDye 800CW was obtained from LI-COR Biosciences (Lincoln, NB). IRDye 800CW reactive dye bears a N-Hydroxysuccinimide (NHS) reactive group to couple primary amines on the antibody and form a stable conjugate. IRDye 800CW in 1× phosphate buffered saline (PBS) has an absorption maximum at 774 nm, emission maximum at 789 nm, and molecular weight of 1166 g/mole. The absorption maxima of the IRDye 800CW corresponds to NIR absorption minima for bodily fluids and tissues and results in enhanced visualization of targeted tumors. The fluorescent signal from the IRDye has a very high signal-to-noise ratio accompanied by low autofluorescence from tissues, cells, biological materials, and drug compounds. Cetuximab was labeled with IRDye as described in the Protein Labeling protocol from LI-COR Biosciences, incubated at room temperature for 1 hour and purified using the Zeba desalting column (Thermo Scientific, Rockford, Ill.). Using spectrophotometric analysis, the ratio of dye-antibody was calculated to be 3.7. Long Chain Succinimidyl 6-(3-[2-pyridyldithio]-propionamido) hexanoate (LC-SPDP), MW=425.52 g/mol, spacer arm length=15.6 Angstroms (Thermo Scientific, Rockford, Ill.), was employed to bioconjugate Cetuximab to gold nanorods. LC-SPDP is a heterobifunctional, thiol-cleavable and membrane permeable crosslinker. LC-SPDP contains an amine-reactive N-hydroxysuccinimide (NHS) ester that reacts with lysine residues to form a stable amide bond on the surface of the antibody. The other end of the spacer arm is terminated in the pyridyl disulfide group that reacts with sulfhydryls to form a reversible disulfide bond with thiol PEGylated gold nanorods.

Exemplary calculations of the crosslinker-antibody molar ratio were performed. For example, the molar ratio of crosslinker to antibody was calculated using the following exemplary methods. The anti-EGFR antibody, Cetuximab, has a molecular weight of 145,782 g/mol used at 2 mg/mL. LC-SPDP crosslinker has a molecular weight of 425.52 g/mol. Calculations were performed by implementing the following:

$$\text{The molarity of the antibody is } \frac{\text{grams of antibody}}{145782 \frac{g}{mol} (\text{MW of antibody})}$$

The molarity of the crosslinker is $$\frac{x \text{ grams of linker}}{425.52 \frac{g}{mol} (\text{MW of linker})} \times \frac{z \text{ }\mu L \text{ (vol of linker in } DMSO)}{y \text{ }\mu L \text{ (vol of } DMSO)}.$$

$$\text{The molar ratio of crosslinker to antibody is } \frac{\text{molarity of linker}}{\text{molarity of antibody}}.$$

The exemplary gold nanorods were fabricated according to the method described herein. Stock Solutions Preparation: For example, 30 mL of HPLC grade water was cooled to 0° C. Solutions of 1 mM Gold (III) chloride trihydrate, ($HAuCl_4 \cdot 3H_2O$), 200 mM cetyltrimethylammonium bromide (CTAB), 78.8 mM Ascorbic acid, and 32 mM $AgNO_3$ were prepared. A hot-water bath, less than 50° C., was used to dissolve CTAB. Ice-cold water was rapidly added to the $NaBH_4$ and the solution was returned to ice. Seeds solution preparation was performed using the following exemplary process. For example, 2.5 mL of 1 mM of $HAuCl_4 \cdot 3H_2O$; 5 mL 200 mM CTAB; and 0.6 mL ice-cold 10 mM $NaBH_4$, were incubated at room temperature (25° C.) for 2 hours before use. Growth solution preparation was performed using the following exemplary process. For example, 20 mL of 1 mM $HAuCl_4 \cdot 3H_2O$ and 20 mL of 200 mM CTAB were combined with various amounts of 32 mM $AgNO_3$, 78.8 mM Ascorbic acid, and of seed solution. The deep pink-colored nanorods were allowed to grow undisturbed for 2 hr at room temperature.

The exemplary gold nanorods were biofunctionalized, e.g., using PEG. For example, the gold nanorods were fabricated with the surfactant, CTAB, as a capping agent to control the size of the nanorod. The process of using poly-ethylene glycol (PEG) to replace the CTAB on the surface of nanorods is known as 'PEGylation' whereby the nanorods are 'PEGylated.' PEGylation is advantageous because it increases biocompatibility and stability, decreases immunogenicity and adsorption to the negatively charged luminal surface of blood vessels, and suppresses the non-specific binding of charged molecules. During the CTAB removal process, the nanorods were centrifuged at (7000 g, 20 min), decanted, and the pellet was resuspended in various amounts of 100 mM PBS. The nanorods were then biofunctionalized, PEGylated, using 1 mM of thiol-terminated methoxy-poly-ethylene glycol (PEG) (MW=5000, Nanocs, New York, N.Y.) and 2 mM of Potassium Carbonate (Acros, Fair Lawn, N.J.) and incubated overnight. A covalent bond was formed between the thiol group of PEG and the surface of the gold nanorod replacing the CTAB. A VersaMax microplate reader was used to determine the relative optical density and concentration of the nanorods. UV-VIS Spectrophotometer was used to calculated the average peak of the absorption spectra as $\lambda=784$ nm. Imaging by Transmission Electron Microscopy (TEM) was used to verify the shape and size consistency of the nanorods.

Antibody conjugation to PEGylated gold nanorods was performed according to the exemplary procedures. For example, PEGylated gold nanorods were conjugated to an exemplary antibody, e.g., Cetuximab, by combining Cetuximab and the LC-SPDP crosslinker in varying molar ratios, desalted, and then added to nanorods that were previously PEGylated. The already biocompatible PEGylated nanorods were crosslinked to the antibodies. Various amounts of the 20 mM crosslinker, LC-SPDP, in DMSO solution was added to Cetuximab and allowed to incubate for 1 hour at room temperature yielding a tunable linker: antibody molar ratio. After the addition of the IRDye, the antibody/cross-linker mix (50-300 μL) was added to the PEGylated nanorods and then incubated at room temperature overnight. Either a Zeba desalt spin column (Pierce Biotechnology, Rockford, Ill.) or a Microcon centrifugal filter device (Millipore, Bedford, Mass.) was used to exchange the buffer from PBS and to remove the reaction byproducts of the PEGylated nanorod-antibody complex.

Exemplary characterizations of the exemplary implementations were performed. For example, gold nanorod-antibody conjugations were examined for structure, consistency, and efficiency by TEM using carbon only copper grids, uranyl acetate stain, and a FEI TecnaiT12 80 kv or 120 kv (Twin TEM, Hillsboro, Oreg.). Digital images of the gold nanorods and conjugates were captured on an AMT 2 k camera (Advanced Microscopy Techniques, Danvers, Mass.). UV-VIS Spectrophotometer was used to measure percent transmittance and calculate the plasmon resonance absorption. A modified ELISA assay was used to evaluate the efficiency of antibody binding before and after conjugation to AuNRs. 500 μL of PBS to recombinant human epidermal growth factor receptor, (EGF R)/ErbB1 Fc Chimera, CF, (50 μg/vial, R&D Systems, Inc., Minneapolis, Minn.) were added for a final concentration of 0.1 mg/mL and used 50 ng/100 μL of recombinant EGFR in PBS w/$Ca^{++}$ and $Mg^{++}$ to coat a 96 well plate. The plate was covered with paraffin and incubated overnight at 4° C. The plate was blocked with 1% bovine serum albumin (BSA) in PBS without $Ca^{++}$ and $Mg^{++}$ to prevent non-specific binding. The samples were incubated for 1 hour at room temperature and analyzed using the Pearl Impulse Imager (LI-COR, Lincoln, NB).

Exemplary implementations of near infrared photothermal therapy were performed. For example, Cal-27, an HNSCC cell line, was maintained in Dulbecco's Modified Eagle Medium containing 10% fetal bovine serum, supplemented with L-glutamine, penicillin, and streptomycin and incubated at 37° C. in 5% $CO_2$. Approximately $1 \times 10^6$ Cal 27 cells/100 μL of serum free media were injected subcutaneously for in vivo experiments. Tumor response was monitored using digital calipers and photography. Tumors were excised at the end of the exemplary implementations to evaluate the effect of AuNRs and the NIR laser separately and combined in comparison to no treatment. Five micron sections of the formalin-fixed, paraffin-embedded blocks were mounted onto slides and heated to 60° C. for 2 hours. The sections were rehydrated in three baths of xylenes and graded alcohols and stained with silver intensification followed by hematoxylin and light eosin.

For example, implementations were performed to evaluate efficacy for the disclosed fluorescently labeled EGFR targeted antibodies, PEGylated gold nanorods and NIR laser irradiation. Gold nanorods demonstrated intrinsic imaging capabilities and were successfully utilized in treatment in vitro, yet the innate visual contrast of the nanorods was severely limited in vivo. The advantages of conjugating antibodies to Cy5.5 dye and IRDye 800CW for fluorescent imaging in vivo have been demonstrated but not in conjunction with photothermal therapies. Exemplary implementations of the disclosed technology included using the anti-EGFR antibody, Cetuximab, which was labeled with IRDye 800CW fluorescent dye and conjugated to gold nanorods. After incubation with the dye-antibody-nanorod conjugate, treatment with NIR light selectively heated the gold nanorods and was sufficient to treat cancers in vitro and reduce tumor size in vivo.

For example, the molar ratio of crosslinker to antibody was varied using the previously described protocol. The effect of crosslinker to antibody molar ratios of 3000:1, 1000:1, 300:1, and 100:1 on the antibody-nanorod conjugation is summarized in FIG. 6. Increasing the molar ratio resulted in a reduction in the space between each nanorod and an apparent increase in clustering. The rate of the conjugation of the gold nanorods to Cetuximab was characterized as a function of clustering by TEM. The count of clustered nanorods was more that 70%.

Figure 6:
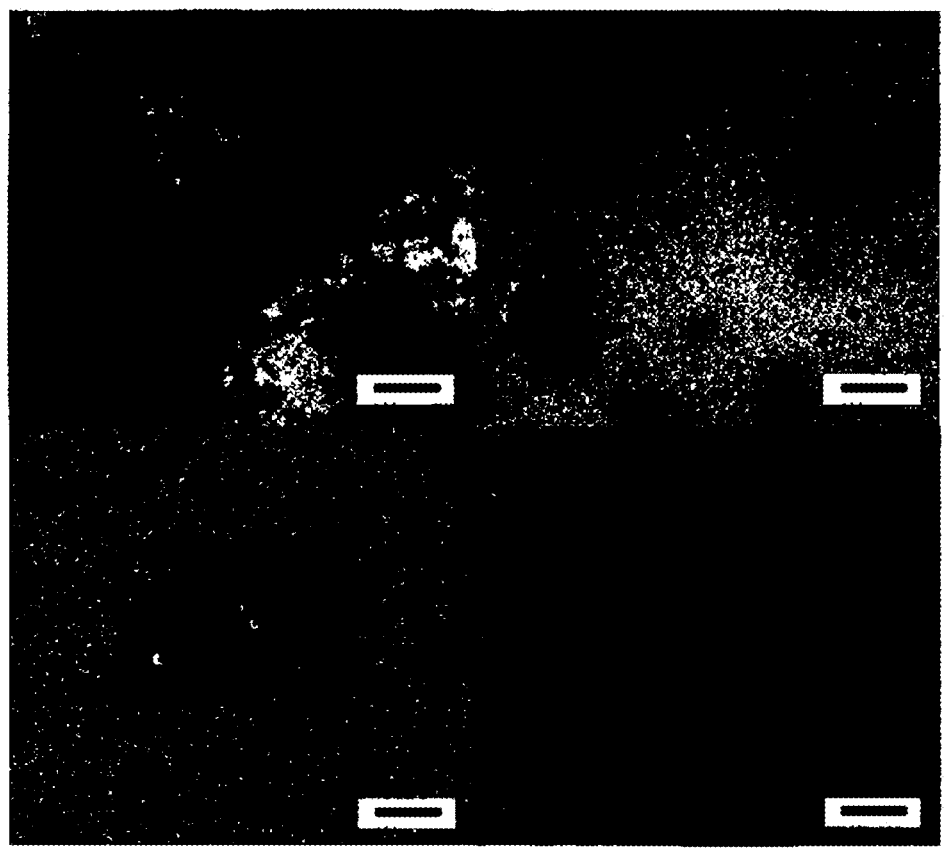
FIG. 6 shows TEM images of exemplary functionalized nanorods with varying crosslinker-antibody molar ratios.

FIG. 6 shows exemplary transmission electron microscope (TEM) images of PEGylated gold nanorods conjugated to anti-EGFR antibody with different LC-SPDP crosslinker-antibody molar ratios, e.g., shown in panels (a) as ~3000:1, (b) as ~1000:1, (c) as ~300:1, and (d) as ~100:1. The exemplary scale bars represent 100 nm.

Transmission electron microscope images were analyzed to determine the cluster frequency of occurrence and the nanorod density within the clusters using a nearest neighbor approach. The nearest neighbor approximation was done by counting nanorods within a circular area with radius, r=2× (nanorod length). A summary of the results for the quantifying the clusters is shown in FIGS. 7A and 7B.

The number of nanorods counted (total number of events) in each of the groups is all-inclusive as to reduce selection bias. This raw data was normalized by only considering 100 events and several observations were made. In FIG. 7A, the nanorod density in a cluster of any size was counted. This calculation takes into consideration that the clusters had various amounts of nanorods. The increase in nanorods clustering that correlates to the increase in crosslinker-to-antibody molar ratio is indicative of a trend that is consistent with the frequency of cluster occurrence in FIG. 7B. The occurrence of nanorods clusters with more than 3 nanorods was analyzed according to the crosslinker-to-antibody ratio used in the conjugation process. The 3000:1 molar ratio group has 38% single rods and 89 occurrences of clusters with more than 3 nanorods. Interestingly, the 1000:1 molar ratio group has 30% single rods, and it has 77 occurrences of clusters with more than 3 nanorods.

Figure 7B:
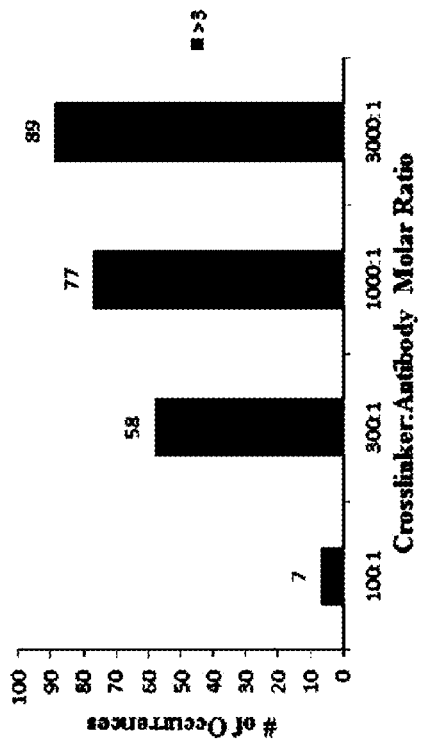
FIGS. 7A and 7B show exemplary data plots of functionalized nanorods with varying crosslinker-antibody molar ratios.
Figure 7A:
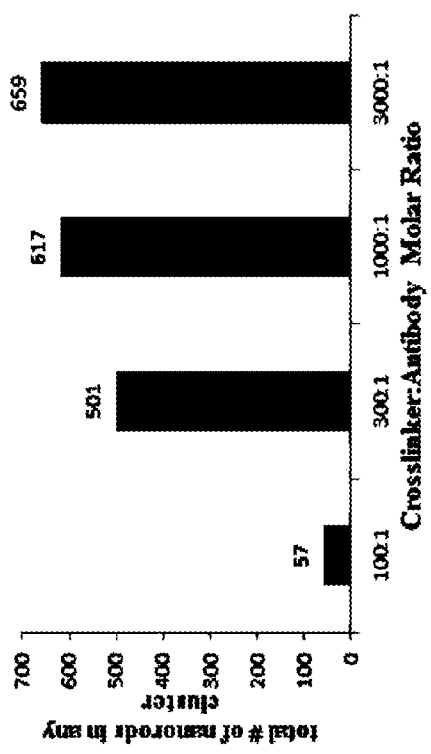

FIGS. 7A and 7B show exemplary data demonstrating a summary of the nearest neighbor analysis of gold nanorods clusters after conjugation for various LC-SPDP crosslinker-to-antibody molar ratios: ~100:1, ~300:1, ~1000:1, and ~3000:1. FIG. 7A shows the nanorod density of the clusters, and FIG. 7B shows the frequency of cluster occurrence. As shown in the figures, the 300:1 molar ratio group has 44% single rods and 58 occurrences of clusters with more than 3 nanorods. The 100:1 molar ratio group has 83% single nanorods and 7 instances of clusters with more than 3 nanorods.

Figure 8:
FIG. 8 shows a TEM image of exemplary functionalized nanorods conjugated to targeting ligand labeled with a fluorescent dye.

The nearest neighbor analysis of the clustering effect of conjugated gold nanorods suggests that nanorod clustering was tuned by varying the crosslinker-to-antibody molar ratio. This nanorod assessment appeared to maintain validity even after the addition of a fluorescent label to the antibody conjugation. FIG. 8 shows the TEM images of gold nanorods conjugated to fluorescently labeled antibodies using a crosslinker-to-antibody molar ratio ~300:1.

FIG. 8 shows exemplary TEM images of PEGylated gold nanorods conjugated to anti-EGFR antibody labeled with fluorescent dye, ~300:1 crosslinker-antibody ratio. The exemplary scale bar represents 100 nm.

This representative sample in FIG. 8 of nanorods conjugated to fluorescently labeled antibodies with ~300:1 crosslinker-antibody ratio shows nanorod clusters comparable to the clusters found in FIG. 6 of nanorods conjugated to antibodies without a fluorescent tag. The integrity of the nanorod shape has not been compromised and the clustering effect of nanorods was maintained after conjugation to fluorescently labeled antibodies. The plasmon resonance absorption of the nanorods was maintained after conjugation to antibodies with and without a fluorescent label.

Figure 9:
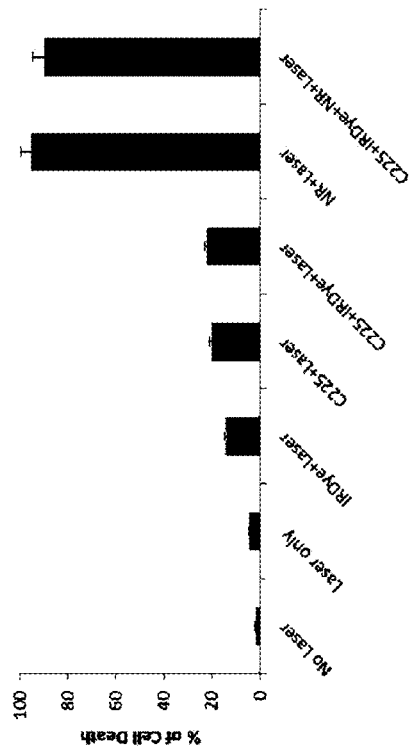
FIG. 9 shows an exemplary data plot of the percentage of cell death after treatment using the disclosed photothermal nanostructure therapy in vitro.

Demonstrating that the nanorods maintain their form and function is essential in maintaining the therapeutic capabilities of near infrared photothermal therapy. The exemplary previous conjugation method showed that the therapeutic effect of the gold nanorods is preserved after conjugation. FIG. 9 compares the therapeutic effect of treatments in vitro.

FIG. 9 shows exemplary data demonstrating the percentage of cell death after treatment in vitro. Cell viability after [left to right] no treatment, laser only, laser plus fluorescent dye (IRDye), laser plus anti-EGFR antibody (C225), laser plus C225 labeled with IRDye, laser plus nanorods, and laser plus nanorods conjugated to IRDye labeled antibody.

The cell viability assay in FIG. 9 shows the difference between the following treatments: no treatment, laser only, laser plus fluorescent dye (IRDye), laser plus anti-EGFR antibody (C225), laser plus C225 labeled with IRDye, laser plus nanorods, and laser plus nanorods conjugated to IRDye labeled antibody. The cell killing effect of the laser without gold nanorods present was minimal regardless of the presence of any variation of antibody or fluorescent dye combination. Conversely, the laser in the presence of nanorods, regardless of fluorescently labeled antibody conjugation, was devastating to the majority of the cells. The therapeutic effect of the gold nanorods was not compromised by the addition of a fluorescent label to the antibody conjugate.

Figure 10A:
FIGS. 10A-10C show exemplary data of fluorescence function of the antibody before and after conjugation to gold nanorods.
Figure 10B:
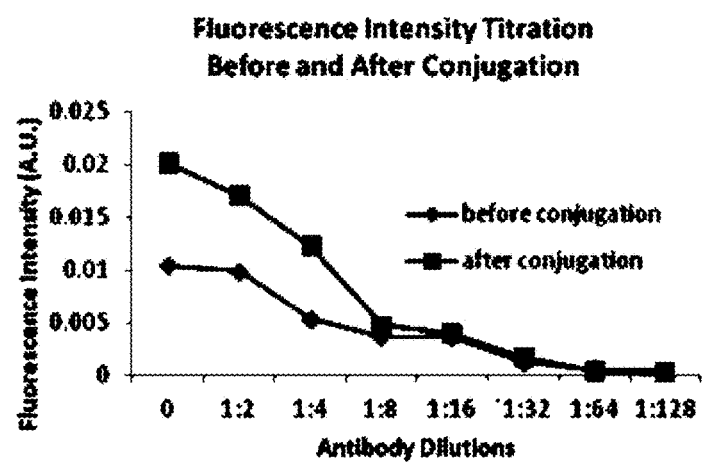
Figure 10C:
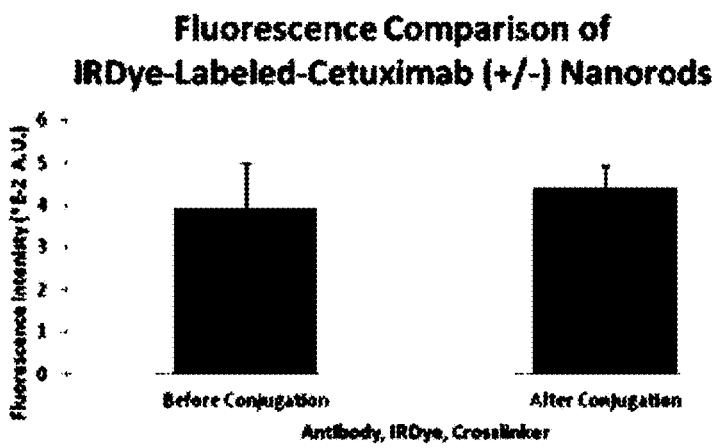

Preserving the therapeutic effect of the nanorods is an important component of expanding the function of PTT to include targeting and imaging. In addition, maintaining the binding ability of the antibody with the fluorescent label is also an important component. FIGS. 10A-10C show exemplary data that compares the fluorescence function of the antibody before and after conjugation to gold nanorods, e.g., comparison of fluorescently labeled antibody before and after conjugation to gold nanorods. FIG. 10A shows exemplary images from a binding assay for fluorescent antibody function before (left) and after (right) conjugaton with gold nanorods. FIG. 10B shows exemplary fluorescence intensity titration assay results. FIG. 10C shows exemplary standardized fluorescence intensity comparison.

Results of previous exemplary implementations showed that the binding function of the antibody before and after conjugation to gold nanorods was maintained, which was consistent with the exemplary current results. The binding ability and fluorescence of the antibodies before conjugation to gold nanorods were comparable to those after conjugation. The binding ability and fluorescence of the antibody indicated that the in vivo targeting ability of the antibody and the imaging capability of the fluorophore would be maintained. The binding ability of the antibody in vitro is not a direct correlation to the targeting function of the antibody in vivo. The result of the disclosed active targeting, fluorescence imaging, and near infrared photothermal treatment is summarized in FIGS. 11A-11G.

FIGS. 11A-11F show exemplary data of active targeting, fluorescence imaging and near infrared photothermal therapy of malignant tumors. FIG. 11A shows an exemplary image on Day 2 after the conjugation injection showing accumulation of the conjugate in the tumor. FIG. 11B shows an exemplary image on Day 3—before laser treatment. FIG. 11C shows an exemplary image on Day 3—after laser treatment. FIG. 11D shows an exemplary image on Day 4—fluorescence returns to the tumor. FIG. 11E shows an exemplary image on Day 8—fluorescent stability. In FIGS. 11A-11E, the featured arrow indicates the tumor. FIG. 11F shows exemplary images of histology data showing silver intensification of gold nanorods in tumor. FIG. 11G shows an exemplary plot demonstrating percent change in tumor volume showing tumor regression after laser irradiation over time.

Exemplary implementations included intravenously injecting gold nanorods conjugated to fluorescently labeled anti-EGFR antibodies. FIGS. 11A-11E show the IRDye labeled of the tumor targeting antibody conjugated to the gold nanorods as it circulates in the mouse. On the second day after the conjugation injection (FIG. 11A), the fluorescence started to accumulate in the tumor in addition to liver, spleen, and kidney. The next day, increased fluorescence in the tumor (FIG. 11B) was observed, which is consistent with the standard circulating time for IRDye labeled antibodies to accumulate in the tumor, ~72 hours. This same time point was chosen for treatment with the NIR laser, after which (FIG. 11C), no fluorescence in the tumor was observed. A day later, the fluorescence returned to the tumor (FIG. 11D) and appeared even stronger four days later (FIG. 11E) indicating the fluorescent antibody has strong accumulation in the tumor. The laser caused the elimination of fluorescence (photo-bleaching) and these results suggest that the conjugated antibody was still circulating in the blood and targeted the tumor again after the laser treatment.

After sacrifice, the presence of gold nanorods in the tumor was confirmed 8 days after intravenous injection (FIG. 11F). This indicates that this protocol for targeted delivery of nanorods enabled long term nanorod accumulation in the tumor, ideal for repeatable laser treatments. In FIG. 11G, regression is shown for a tumor targeted with a dye-antibody-nanorod conjugate followed by a 10 minute NIR laser treatment. As is standard with all cancer treatments, the tumor will eventually continue to grow unless it is completely eliminated. This was the case 4 days after PTT, a partially reduced tumor started to re-grow, e.g., which can be used as an exemplary time point to initiate an additional treatments.

The optimized antibody-to-nanorod conjugation molar ratios disclosed were used in exemplary implementations which were shown to enable sufficient in vivo tumor targeting and resulted in a reduction in tumor size. In addition to decreasing tumor volume, the disclosed active targeting and fluorescent imaging modalities were implemented with near infrared photothermal therapy.

For example, the described technology demonstrated that manipulating the molar ratio of the cross linker to antibody, and the order of PEGylation and conjugation, can improve active tumor targeting with antibodies and near infrared photothermal therapy. The exemplary data indicated that gold nanorods maintained their therapeutic ability even after conjugation to a fluorescently labeled antibody. The disclosed techniques were shown to be minimally invasive and repeatable for actively targeting, fluorescently imaging, and using near infrared photothermal therapy that can result in tumor reduction. The disclosed technology can also include optimizing delivery and treatment parameters, incorporating antibody drug conjugates, and combining treatment with the current standards of care. For example, the disclosed selective targeting, imaging and photothermal treatments can be implemented in a variety of cancer types, including squamous cell carcinomas.

In another aspect of the disclosed technology, systems, devices, materials, and techniques are disclosed for photothermal therapy using a targeted systemic delivery of nanoparticles and light energy to a tissue site (e.g., a tumor), e.g., by directly injecting nanoparticles into the tumor. Exemplary implementations include evaluation of the tumor reduction effects resulting from the combination of a one-time 10-minute NIR laser treatment and a direct intratumoral injection of gold nanorods.

Exemplary processes, methods, and techniques for predictive calculation of parameters for PTT based on tumor model are disclosed. For example, a locally destructive quantity of heat is generated from the excitation of gold nanorods by NIR light irradiation with a wavelength overlapping with gold nanorod plasmon resonance absorption. Based on the rate of heat deposition to the tumor, Q, that is needed to cause damage, a protocol was outlined to calculate the laser output power, P, and the gold nanorod concentration in the tumor, $N_{AuNR}$.

Figure 12A:
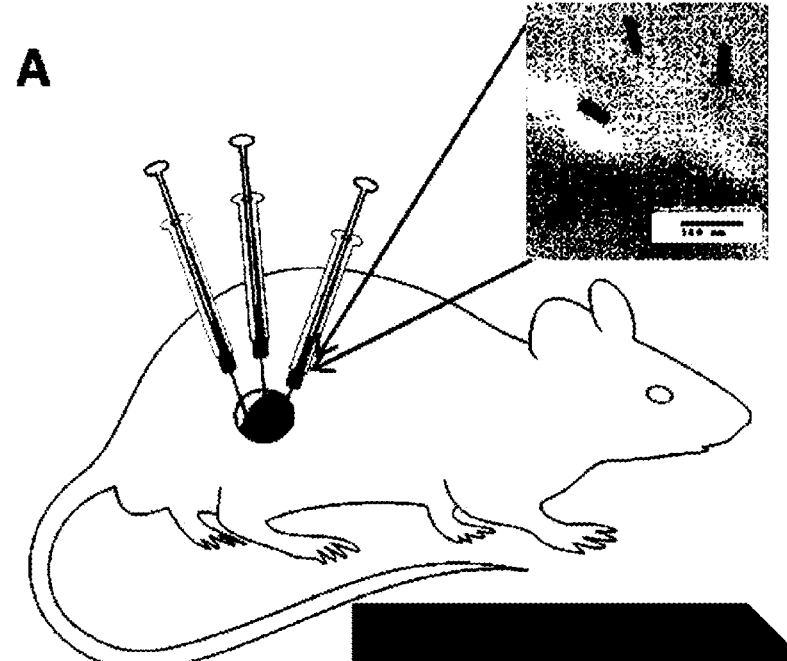
FIGS. 12A-12C show exemplary schematic illustrations of an exemplary injection and laser irradiation method.
Figure 12B:
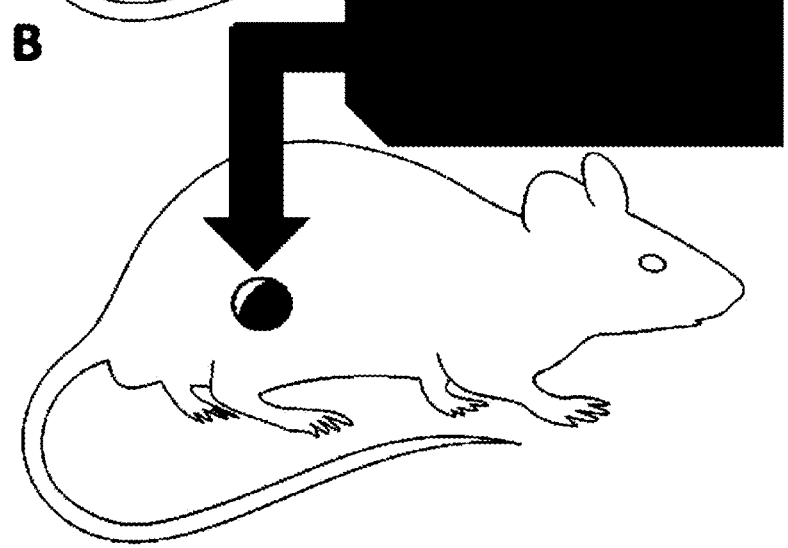
Figure 12C:
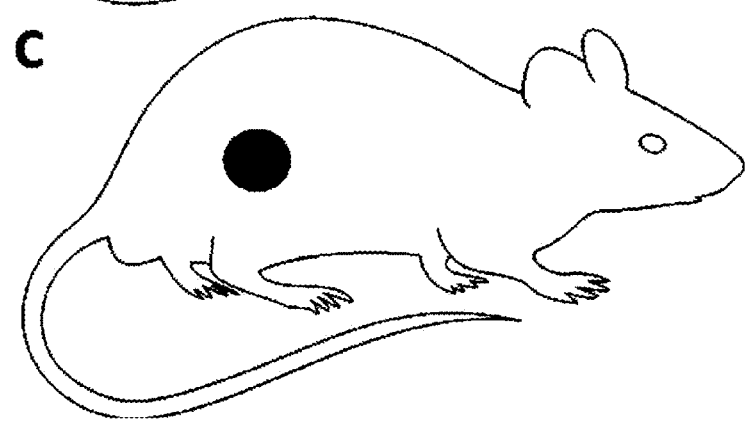

As shown in FIGS. 12A-12C, an exemplary tumor was modeled as an isothermal sphere, diameter D=5 mm, buried in a semi-infinite tissue beneath the skin. The distance between the center of the tumor and the skin surface was Z=5.5 mm. The rate of heat dissipated, $\dot{Q}$ to the tumor of diameter D, was approximated using the solution of a heat transfer problem based on conduction of heat involving two surfaces maintained at constant temperatures, the tumor temperature, $T_1$=333 K and the temperature of the skin, $T_2$=309 K. It is known that temperatures between 316 K and 333 K damage the cell originating from protein denaturation and temperatures above 333 K result in tissue coagulation. This type of heat transferred were analytically solved in where it was shown that the steady rate of heat dissipated can be described by $\dot{Q}=Sk(T_1-T_2)$, where the coefficient of thermal conductivity of the tissue was k=0.2 W/mK and the conduction shape factor, $$S = \frac{2\pi D}{1 - 0.25\, D/Z} = 0.04\, m,.$$

For example, in a steady state condition, the rate of photo-generated heat deposited in the tumor is equal to the rate of heat dissipation from the tumor due to conduction. Hence, $\dot{Q}=PA$ where the incoming laser radiation absorption of the nanorods in the tumor, $A=1-T_{transmittance}$, was assumed to be 80%. From this equation, the value of laser power necessary to heat the tumor to required temperature 333K was $$P = \frac{sk(T_1 - T_2)}{A} = 0.24\, W.$$

The cross section of absorption of gold nanorods, $\sigma_a$=5.5×$10^{-11}$ cm$^2$, with appropriate aspect ratio ~4 was obtained from the cross section of extinction for gold nanorods $\sigma_{ext}=\sigma_{abs}+\sigma_{scat}$=6×$10^{-11}$ cm$^2$ and $$\frac{\sigma_{abs}}{\sigma_{scat}} = 0.1.$$

The calculated concentration of nanorods in the tumor enabling 80% absorption of incoming light was $$N_{AuNR} = \frac{\ln(1-A)}{-\sigma_a D} = 5.85 \times 10^{10} \text{ cm}^{-3}.$$

The needed concentration of gold nanorods in a solution with a volume, $V_{solution}=50$ µL, was calculated by using the concentration of gold nanorods needed in the tumor with a volume, $V_{tumor}=0.065$ cm$^3$=65 µL:

$$Nsolution = \frac{N_{AuNR} \times V_{tumor}}{V_{solution}} = 7.6 \times 10^{10} \text{ cm}^{-3}.$$

The concentration of gold nanorods in a 50 µL solution needed to photothermally increase the tumor temperature to 333 K using 240 mW NIR laser output power was $7.6 \times 10^{10}$ cm$^{-3}$ ($7.6 \times 10^{10}$ nanorods/mL). This approximation was used to guide the experimental parameters for the in vivo near infrared photothermal therapy.

Exemplary implementations were performed to demonstrate the disclosed predictive calculations model. The exemplary implementations included the fabrication and functionalization of gold nanorods, e.g., summarized as follows. Stock Solutions Preparation: 30 mL of HPLC grade water was cooled to 0° C. Solutions of 1 mM Gold (III) chloride trihydrate, (HAuCl$_4$·3H$_2$O) (Sigma-Aldrich, St. Louis, Mo.), 200 mM cetyltrimethylammonium bromide (CTAB) (Sigma-Aldrich, St. Louis, Mo.), 78.8 mM Ascorbic acid, and 32 mM AgNO$_3$ (Sigma-Aldrich, St. Louis, Mo.) were prepared. A hot-water bath, less than 50° C., was used to dissolve CTAB in solution. Ice-cold water was rapidly added to the 10 mM NaBH$_4$ and the solution was returned to ice. Seeds Solution Preparation: 2.5 mL of 1 mM HAuCl$_4$·3H$_2$O; 5 mL of 200 mM CTAB; and 0.6 mL of ice-cold 10 mM NaBH$_4$, were incubated at room temperature (25° C.) for 2 hours before use. Growth Solution Preparation: 20 mL of 1 mM HAuCl$_4$·3H$_2$O and 20 mL of 200 mM CTAB were combined with various amounts of 32 mM AgNO$_3$, 78.8 mM Ascorbic acid, and seed solution. Once the solution color was a deep pink, the nanorods were allowed to grow undisturbed for 2 hours at room temperature.

Gold nanorods were fabricated with the surfactant, CTAB, as a capping agent to control the size of the nanorod. Poly-ethylene glycol (PEG) replaced the CTAB on the surface of nanorods in a process known as 'PEGylation' whereby the nanorods are 'PEGylated.' PEGylation was advantageous because it increased nanorod biocompatibility and stability, decreased immunogenicity and adsorption to the negatively charged luminal surface of blood vessels, and suppressed the non-specific binding of charged molecules. During the CTAB removal process, the nanorods were centrifuged (7000 g, 20 min), decanted, and the pellet was resuspended in various amounts of 100 mM PBS depending on tumor size. The nanorods were then biofunctionalized, PEGylated using 1 mM of thiol-terminated methoxy-polyethylene glycol (PEG) (MW=5000, Nanocs, New York, N.Y.) and 2 mM of Potassium Carbonate (Acros, Fair Lawn, N.J.) and incubated overnight. A covalent bond was formed between the thiol group of PEG and the surface of the gold nanorod replacing the CTAB. A VersaMax microplate reader was used to determine the relative optical density and concentration of the nanorods. The measured range of concentrations of the PEGylated nanorods was CONC$_{PEG-NR}$=1.12–4.41 mg/mL. The range of optical densities of the PEGylated nanorods was OD$_{PEG-NR}$=2.06–8.24 (~3.75× $10^{10}$–1.50×$10^{11}$ AuNRs/mL) and the solution with O.D.=4.18 (7.6×$10^{10}$ AuNRs/mL) was utilized in the majority of experiments. The average peak of the plasmon resonance absorption maximum of different batches of gold nanorods was λ=784 nm as measured by UV-VIS-NIR Spectrophotometer. Gold nanorods were examined for structure, consistency, and efficiency by Transmission Electron Microscope (TEM) using carbon only copper grids, uranyl acetate stain, and a FEI TecnaiT12 80 kv or 120 kv (Twin TEM, Hillsboro, Oreg.). Digital images of the gold nanorods and conjugates were captured on an AMT 2 k camera (Danvers, Mass.). UV-VIS-NIR Spectrophotometer was used to measure percent transmittance and calculate the plasmon resonance absorption maxima.

For example, Cal 27, a head and neck squamous cell carcinoma (HNSCC) line, was maintained in Dulbecco's Modified Eagle Medium containing 10% fetal bovine serum, supplemented with L-glutamine, penicillin, and streptomycin and incubated at 37° C. in 5% CO$_2$. Approximately $1 \times 10^6$ Cal 27 cells/100 µL of serum free media were injected subcutaneously for in vivo experiments and allowed to grow until tumor reached ~5 mm in diameter.

The tumor was radially injected at multiple sites with PEGylated nanorods, 10-50 µL. Photothermal therapy of tumors was performed within thirty minutes of AuNR injection. A continuous wave NIR semiconductor diode laser (SDL, Inc, San Jose, Calif., 8350) was used to irradiate the tumors for a single 10-minute exposure time, 785 nm wavelength, 9.5 W/cm$^2$ fluence (e.g., illustrated in FIGS. 12A-12C). The beam diameter was adjusted to be approximately equal to the diameter of the tumor.

FIGS. 12A-12C show exemplary schematic illustrations of the disclosed injection and laser irradiation method. For example, FIG. 12A shows multiple intratumoral injections of PEGylated gold nanorods (inlet: the TEM images of gold nanorods) followed by, as shown in FIG. 12B, a 10-minute near infrared laser irradiation of tumor and resulting in, as shown in FIG. 12C, tumor discoloration eventually leading to tumor regression.

Tumor response was captured with photography, measured with digital calipers and calculated based on the change from the original volume. Exemplary implementations also include utilizing euthanized mice and removing tumors or remaining scars to evaluate the combined effect of AuNRs and the NIR laser in comparison to the control groups: no treatment, laser only, and AuNRs only. For histology, five micron sections of the formalin-fixed, paraffin-embedded blocks of were mounted onto slides and heated to 60° C. for 2 hr. The sections were rehydrated in three baths of xylenes and graded alcohols and stained with silver intensification followed by hematoxylin and light eosin.

Figure 13:
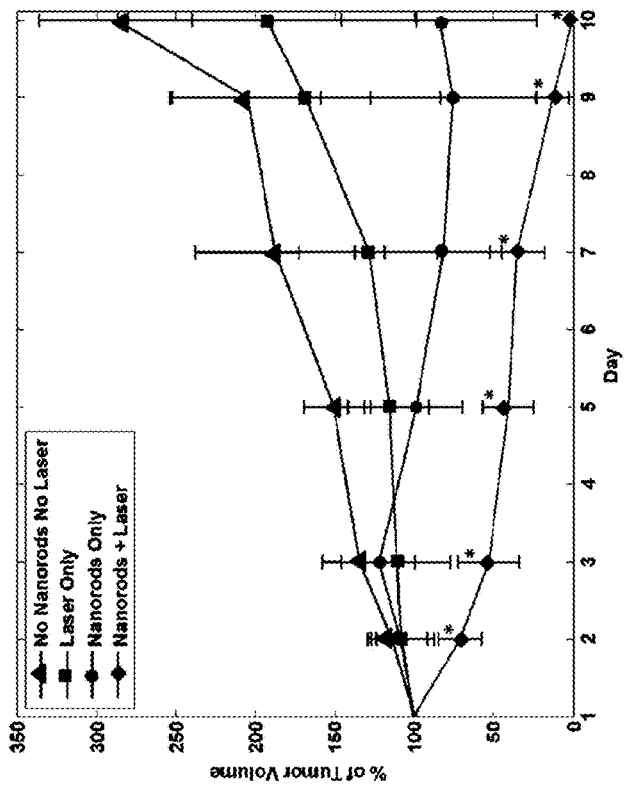
FIG. 13 shows an exemplary data plot of tumor regression comparing treatment techniques.

The combined effect of directly injecting gold nanorods into subcutaneous tumors followed by a single 10-minute treatment with NIR light caused tumor regression. The overlap in the NIR spectral range of the laser emission wavelength and the plasmon resonance absorption resulted in rapid electron oscillation and subsequent local heat generation transferred to the surrounding tumor. The consequent tumor growth rates, resulting from no treatment (n=4), laser only (n=4), AuNRs only (n=3), and the combination of AuNRs and laser treatment (n=6), were compared. The tumor sizes were normalized on day 1 as 100% and any growth or regression was taken as change from the initial volume. FIG. 13 shows the measured change in tumor volume over 10 days under different treatment conditions. The observable differences in each of the treatment groups were further analyzed for statistical significance on each day, shown in Table 1, and on day 10 with histology, shown in FIG. 14.

A statistically significant difference in the tumor volume was observed after an intratumoral gold nanorod injection and one 10-minute laser irradiation, as compared to the control groups starting on the day after treatment (day 2), and was maintained for the duration of the implementation. The combination treatment resulted in gradual tumor regression and an apparent elimination of the tumor.

Table 1 shows exemplary p-values of a one-way analysis of variance (ANOVA) of the combination of gold nanorods and NIR laser irradiation treatment as compared to the other treatment groups at different days. $p<0.05$ indicates a significant difference between groups, denoted by *.

FIG. 13. The histology of these representative resected tumors (FIG. 14) was evaluated by a board certified pathologist (WEG).

Figure 14:
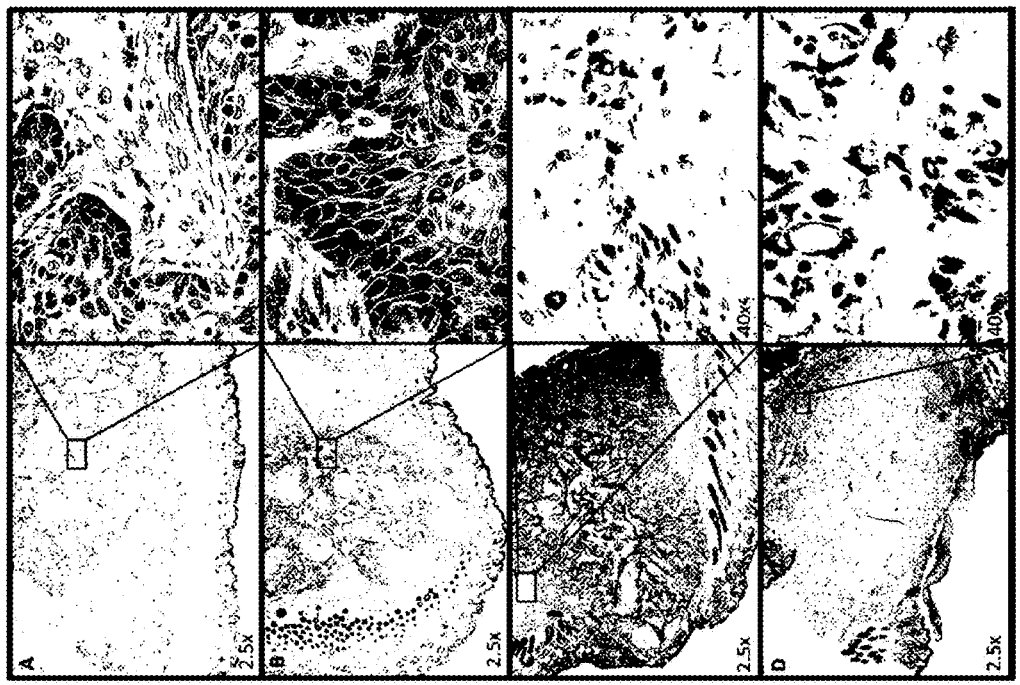
FIG. 14 shows histology images of representative tumors resected comparing exemplary treatment groups.

FIG. 14 shows exemplary histology data of representative tumors resected 10 days comparing all treatment groups. FIG. 14 panel (A) shows the no treatment group, e.g., showing viable tumor tissue. FIG. 14 panel (B) shows the laser only group, e.g., showing viable tumor tissue. FIG. 14 panel (C) shows the nanorods only group, e.g., showing mostly viable tumor tissue. FIG. 14 panel (D) shows the combination treatment group, e.g., showing no tumor, scar tissue and inflammatory cells. The exemplary color delineation in FIG. 14 include, e.g., hematoxylin (blue) stains for nuclei, eosin (pink) stains for cytoplasm, and silver intensification (black) stains for gold nanoparticles indicated by arrows.

The resected tumor from the no treatment group, FIG. 14 panel (A), was used as the standard to identify the structure of viable tumor and the biological noise present throughout the treatment groups. The tumor characteristics include tightly compacted cells with clear cell boundaries indicating intact cytoplasm (pink) around a nucleus (purple). The presence of mitosis indicates tumor proliferation yet some

|  | Day | | | | | | |
| --- | --- | --- | --- | --- | --- | --- | --- |
|  | 1 | 2 | 3 | 5 | 7 | 9 | 10 |
| Nanorods + Laser vs. No Treatment | NaN | 0.0009* | 0.0008* | <0.0001* | 0.0004* | <0.0001* | <0.0001* |
| Nanorods + Laser vs. Laser Only | NaN | 0.0199* | 0.0201* | 0.002* | 0.0044* | 0.0052* | 0.0028* |
| Nanorods + Laser vs. Nanorods Only | NaN | 0.0127* | 0.0039* | 0.0099* | 0.0473* | 0.0324* | 0.0178* |

FIG. 13 shows exemplary data demonstrating a summary of tumor regression over 10 days comparing the combination treatment to the control groups. The * indicates a statically significant difference between groups. The exemplary error bars are from standard deviation, plus and minus one standard deviation.

The tumor volume in the no treatment group increased to nearly triple the original volume. The tumors sustaining a 10-minute NIR laser treatment, in the laser only group, grew to approximately double the original volume, displaying modified growth patterns. The difference between the laser only and the no treatment groups was not statistically significant, e.g., NIR light can be considered completely benign because it did not cause cell death.

The tumors directly injected with PEGylated gold nanorods without any laser exposure (nanorod only) showed inhibited growth patterns, roughly maintaining the original volume. The nanorod only treatment group did not display the growth patterns observed in the other control groups, yet the volume was significantly larger than the combination treatment group. These exemplary results were inconsistent with the in vitro results previously described that confirmed the non-cytotoxic behavior of PEGylated gold nanoparticles. In retrospect, an intratumoral saline injection treatment group would have provided insight into the effects observed in the nanorod only group. It is possible that the injection itself, not the nanorods, inhibited tumor growth by providing injury to a blood vessel thus limiting the nutrient supply necessary for viable tumor growth.

Further examination provides insight into the microscopic consequences of each of the treatment groups measured in intrinsic tumor death indicates ischemia generally caused by complications with blood vessels, resulting in damage to the tissue (inset image of FIG. 14 panel (A)).

The characteristics of the laser only tumor are consistent to the general characteristics of the no treatment tumor (FIG. 14 panel (B)) showing mitosis and intact nuclei and cytoplasm (inset image of FIG. 14 panel (B)). With the assumption that the PEGylated AuNRs are biologically inert, the damage shown in FIG. 14 panel (C) can be attributed to the superficial blood vessel injury likely due to the injection puncture, not the nanorods. This may be the reason for a lack of mitotic cell occurrence as well. There is a tract of gold nanorods (inset image of FIG. 14 panel (C)) in an area of disruption near the disturbed blood vessels. This assumption is further supported by the consistency of the rest of the tumor with the structure found in FIG. 14 panels (A) and (B) of the no treatment and laser only treatment groups, respectively.

After the combination treatment, the remains of the tumor were found in the area under the scab and examined for histology (FIG. 14 panel (D)). It appears that there was no residual tumor; the epithelial and hair follicles were damaged; and scar tissue, areas of repair, and inflammatory cells, instrumental in the healing process, were present. The structures of the tumor remnants (inset image of FIG. 14 panel (D)) were very different from the compacted cells of the viable tumor in FIG. 14 panels (A) and (B) and nanorods were visible in the area of damage.

For example, tumor recurrence may be reduced when the tumor is treated at the root, e.g., analogous to weeds in a garden. With PTT, similar to other treatments, it is most effective if the tumor is completely treated especially at the interface with healthy tissue. The disclosed technology may be used to address tumor regrowth, for example, as tumor regrowth is still important to treat the whole tumor and the root to see dramatic tumor regression and to reduce recurrence potential.

Significant tumor reduction was observed after the combination treatment of AuNRs and laser but was not observed for any other treatment group. Various amounts, 10-50 µL, of the working concentration of AuNRs were injected into the tumor followed by the 10-minute laser treatment. There were no observable differences in tumor regression for different volumes of AuNRs used thus no dose curve was established here. The photographic images in FIG. 15 panels (A)-(N) capture the rapid disintegration of the tumor after direct injection with gold nanorods followed by a one-time 10-minute laser treatment. These photographs were taken at the on the first day, before and after treatment, then daily until the 15$^{th}$ day after treatment. The tumor experienced immediate discoloration after treatment. The days after the laser treatment showed continued tumor regression and healing. This was representative of all of the tumors treated in conducted tests.

Acute damage was observed for the combination treatment reaching temperatures of ~60° C. The external appearance of black discoloration of the tumor was likely due to the blood from thermally disrupted vessels.

FIG. 15 shows exemplary photographic images of mouse tumor. In FIG. 15, panel (A) shows Day 1 before treatment; panel (B) shows Day 1 after treatment with directly injected PEGylated gold nanorod and one time 10 minute NIR laser irradiation; panel (C) shows Day 2; panel (D) shows Day 3; panel (E) shows Day 4; panel (F) shows Day 5; panel (G) shows Day 6; panel (H) shows Day 7; panel (I) shows Day 8; panel (J) shows Day 9; panel (K) shows Day 10; panel (L) shows Day 11; panel (M) shows Day 13; and panel (N) Day 15. The width of the exemplary cropped pictures is 19.05 mm (0.75 in.).

The tumor on the day after treatment, as presented in FIG. 15 panel (C), correlates to FIG. 16A which shows the histology of abrupt tumor damage. The tumor indicates coagulation and damage to the skin and hair follicles. The level of cellular destruction is obvious in FIG. 16A inlet which highlights the blood vessel damage and the red blood cells in the tumor.

FIGS. 16A and 16B show histology images of tumor directly injected PEGylated gold nanorod with laser treatment excised at different time points after treatment day 2 (as shown in FIG. 16A) and treatment day 15 (as shown in FIG. 16B). Exemplary arrow indicates nanorods inside macrophage cell.

For example, it is likely that the destruction of blood vessels (e.g., leading to apoptosis), in addition to the immediate temperature damage (e.g., leading to necrosis), may cause the continued tumor reduction that was observed over the duration of the implementation. The corresponding histology of the tumor from 15 days after the single combination treatment (FIG. 15 panel (N)) is shown in FIG. 16B. For example, there is no indication of viable tumor; only inflammatory cells, scar tissue and intact skin. The presence of macrophages (brown) appearing to contain gold nanorods and red blood cells is an indication of necrotic debris removal and repair.

There were several mechanistic variations of the combination treatment that resulted in tumor regression. The combination of the nanorods and laser was local; exposing only half of a uniformly injected tumor to the NIR laser resulted in regression of the laser treated half of the tumor. Compromised effects of the injection dose were not observed by using different volumes or concentrations of nanorods. The nanorod distribution throughout the tumor and the appropriate diameter of the laser were essential in obtaining uniform results. After receiving the combination treatment, 8 of the 10 tumors showing ~100% regression, as measured by calipers, were deemed tumor free by histology.

FIG. 17 shows exemplary histology images of tumor present after combination treatment of direct injection of PEGylated gold nanorods and 10 min NIR laser irradiation, showing scar tissue, inflammatory cells, gold nanorods, and both damaged and viable tumor. The exemplary arrow indicates silver intensification of gold nanorods in region of damage.

In the other 2 cases, the external appearance was of tumor regression, scaring and healing but histology showed the regeneration of the skin, epithelial, fat, and muscle, as well as viable tumor under the scar (FIG. 17). These outcomes indicate that the nanorod distribution throughout the tumor, especially at the root, was not sufficient since the irradiation diameter was slightly larger than the tumor diameter, marginally treated tumor was adjacent to an area of damage, and an abundance of nanorods were present in the treated area (inlet image of FIG. 17). The evidence was insufficient to confidently determine whether the post-treatment presence of the tumor was due to a lack of regression or a local recurrence. In the majority of cases (8 of 10), one combination treatment was adequate to obtain complete tumor regression without incident of recurrence within 10-15 days. The other 2 cases, even without uniform nanorod distribution, would have benefited from more than one laser treatment.

Described is an exemplary protocol to calculate the concentration of exemplary nanorods and output power of the laser, e.g., based on a disclosed conductive model of heat dissipation from the tumor. Implementations of the exemplary conductive model of heat dissipation from the tumor were performed and found to be in agreement with exemplary PTT experimental results. For example, ~100% reduction in tumor volume was demonstrated from implementation of direct gold nanorod injections followed by a one-time 10 minute laser treatment. This exemplary technique of gold nanorod and laser therapy resulted in statistically significant tumor reduction in comparison to the control groups: no treatment (p<0.0001), laser only (p=0.0028), and gold nanorod only (p=0.0178) 10 days after treatment. The described exemplary implementations used exemplary oral squamous carcinoma and demonstrated efficacy of the intratumoral injection of gold nanorods and subsequent photothermal treatment of tumors approach, e.g., which can be applied for a variety of carcinomas. For example, other exemplary tumors to implement the disclosed technology can include head and neck, colorectal, ovarian, skin, cervical, breast, bladder, pancreatic, and prostate cancers, e.g., because they are readily scope accessible and within the 10 cm penetration depth of NIR light. For example, the disclosed technology can provide an effective tumor therapy treatment for primary and early stage tumors, and can also be implemented in combination with early detection and imaging mechanisms. The disclosed technology can also be used in clinical applications, e.g., in which the disclosed nanoparticles and PTT may be used in combination with drug conjugates and the current standards of care.

Figure 18A:
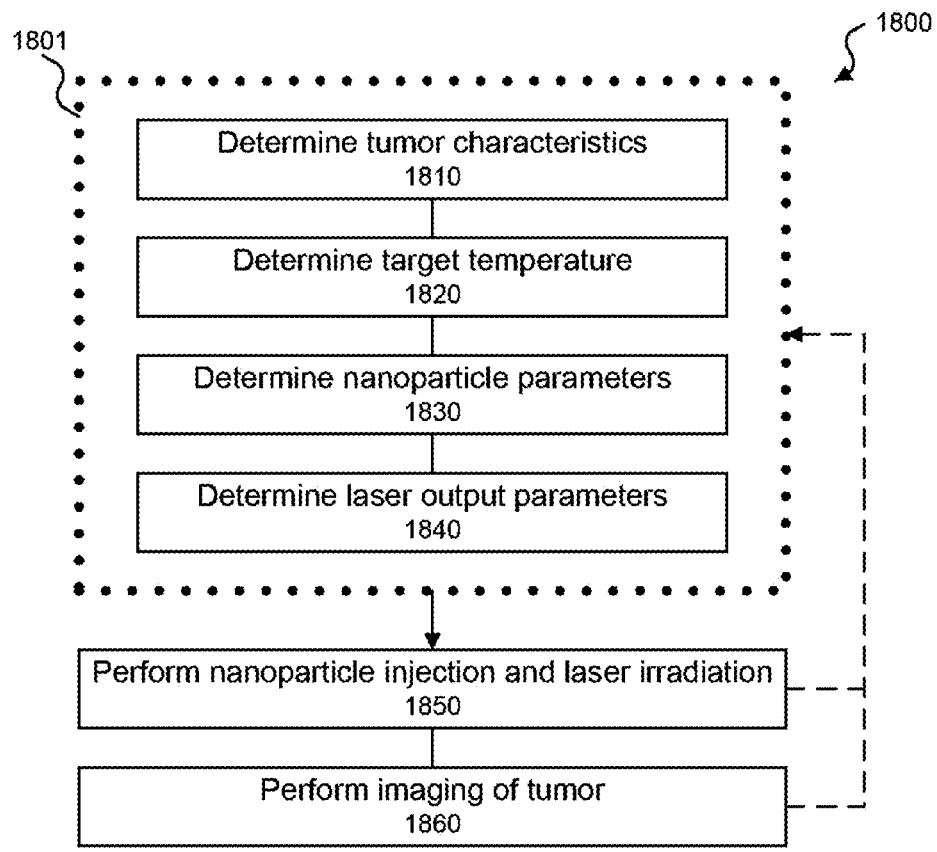
FIG. 18A shows an exemplary protocol for photothermal therapy based on the predictive calculations of the disclosed technology.

FIG. 18A shows a process 1800 of an exemplary protocol for photothermal therapy based on the predictive calculations of the disclosed technology. The process 1800 includes a process 1801 to implement the predictive calculations of the disclosed technology that can be used in performing a photothermal therapy of the disclosed technology. The process 1801 can include a process 1810 to determine tumor characteristics, a process 1820 to determine the target temperature to produce at the tumor, a process 1830 to determine the nanoparticle parameters, and a process 1840 to determine the laser output parameters. The process 1800 can also include a process 1850 to perform nanoparticle injection and laser irradiation and/or a process 1860 to image the tumor, e.g., based on implementation of process 1801. The process 1800 can also include repeating the process 1801 before, during, or after implementation of the process 1850 or the process 1860. The processes 1810, 1820, 1830, and 1840 of the process 1801 can be performed in the exemplary sequence described in FIG. 18A, or in other sequences not shown in the exemplary figure.

Figure 19:
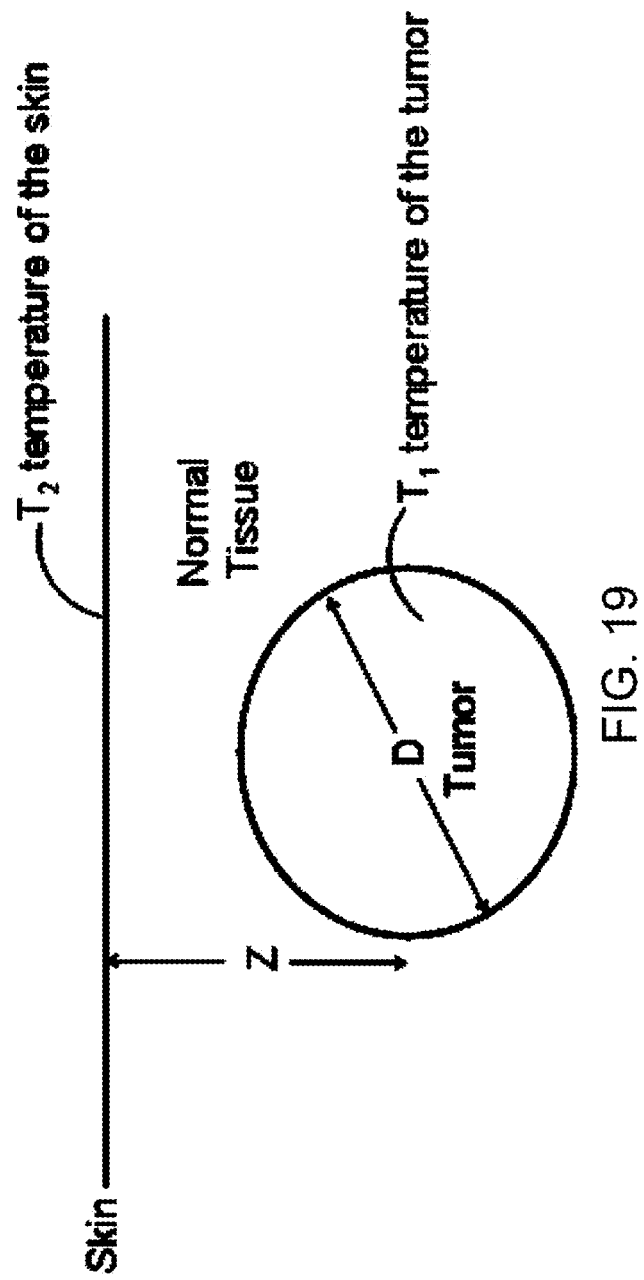
FIG. 19 shows an exemplary tumor model used in the exemplary predictive calculations model for photothermal therapy.

For example, the process 1810 can include characterizing the diameter (D) of the exemplary tumor, volume ($V_{tumor}$) of the exemplary tumor, shape (S) of the exemplary tumor, and depth of the exemplary tumor beneath the skin (Z). For example, FIG. 19 shows an exemplary tumor model that can be used in process 1810 of the exemplary predictive calculations for photothermal therapy.

For example, the process 1820 can be implemented to determine the target temperature to produce the desired effect on the tumor, e.g., to induce tumor death. For example, the process 1820 can include determining the target tumor temperature ($T_1$) used for the desired treatment effect (e.g., protein denaturation, coagulation, and/or carbonization).

Figure 18B:
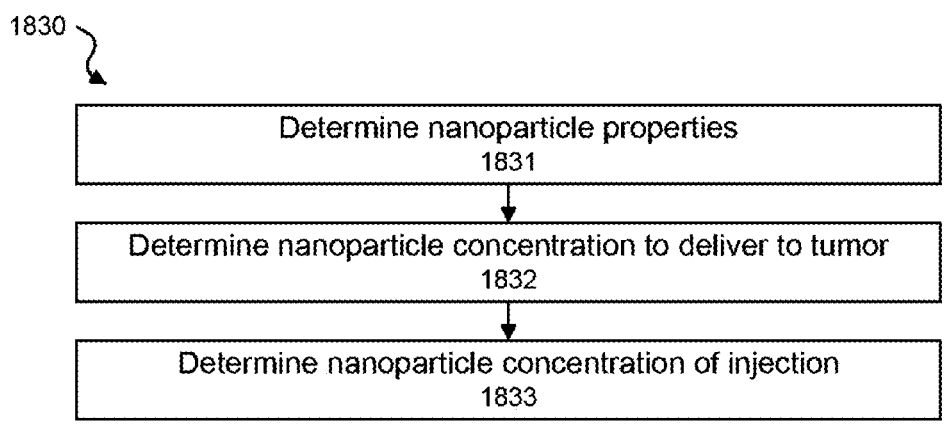
FIG. 18B shows an exemplary process to determine the nanoparticle parameters for photothermal therapy.

For example, the process 1830 can include a process 1831, a process 1832, and a process 1833, shown in FIG. 18B. The process 1831 can include determining nanoparticle properties, e.g., in which exemplary nanoparticle properties can include type or shape (e.g., rods, spheres, cones, cages, cubes, tubes, as well as other shapes), size, material (e.g., gold, silver, iron, carbon, silicon, as well as other materials), aspect ratio (e.g., length/diameter), and value of the cross-section of absorption. The process 1831 can include determining the cross-section of absorption of the designed nanoparticle. For example, the process 1831 can include configuring the nanoparticle to have a plasmon resonance absorption to overlap with the laser emission wavelength (e.g., used for photothermal therapy), e.g., which can enable interaction selectivity between the nanoparticle and the laser based on the characteristics of the nanoparticle. For example, the nanoparticle parameters can be configured to have a plasmon resonance peak at 785 nm, a wavelength to which a near infrared laser emission wavelength for a photothermal therapy application can also be configured. This exemplary configuration can be optimal in terms of the large depth of penetration through both normal and tumor tissue, as well as for fabrication of exemplary gold nanorods at a specific size, e.g., a 4:1 aspect ratio. The process 1832 can include determining nanoparticle concentration to deliver to the exemplary tumor. For example, the process 1832 can include calculating the nanoparticle concentration in the tumor, e.g., $$N_{NP} = \frac{1}{\sigma_a D} \ln \frac{1}{1-A},$$

based on 50-100% nanoparticle absorption of light through the exemplary tumor, A, and cross-section of absorption for the nanoparticle. The process 1833 can include determining nanoparticle concentration of the exemplary injection solution. For example, the process 1833 can include calculating the nanoparticle concentration of the exemplary injection solution, e.g., $$N_{solution} = \frac{N_{NP} \times V_{tumor}}{V_{solution}}.$$

For example, the process 1840 can include calculating the laser output power, e.g., $$P = \frac{Sk(T_1 - T_2)}{A},$$

using the heat dissipation analysis for conductivity model and the conductive shape factor, e.g., $$S = \frac{2\pi D}{1 - 0.25 \; D/Z}$$

for a spherical tumor.

For example, the process 1850 can include performing a uniform distribution injection and laser irradiation to enable treatment of tumor, e.g., including tumor margins. For example, the process 1860 can include imaging the tumor, e.g., using fluorescent imaging of the fluorophore-conjugated functionalized nanoparticles (e.g., PEGylated nanorods conjugated to targeting ligands). In some examples, the use of magnetic resonance imaging (MRI) can be used to implement the process 1860. The process 1800 can include implementation of process 1850 while not implementing the process 1860, and in turn the process 1800 can include implementation of process 1860 while not implementing the process 1850.

Exemplary methods, processes, and techniques described in the process 1801 to disclosed photothermal therapy using nanoparticles can be performed on systems and devices, e.g., a computerized system that can perform the predictive calculations of the process 1801, and in some examples, also control the laser irradiation and imaging systems in the process 1800. For example, the exemplary computerized system can include a processor that can be in communication with an input/output (I/O) unit, an output unit, and a memory unit. The exemplary processing unit can be implemented as one of various data processing systems, such as a personal computer (PC), laptop, tablet, and mobile communication device. To support various functions of the exemplary processing unit, a processor can be included to interface with and control operations of other components of the processing unit, such as the exemplary I/O unit, the exemplary output unit, and the exemplary memory unit.

To support various functions of the processing unit, memory unit can store other information and data, such as instructions, software, values, images, and other data processed or referenced by the processor. Various types of Random Access Memory (RAM) devices, Read Only Memory (ROM) devices, Flash Memory devices, and other suitable storage media can be used to implement storage functions of memory unit. The exemplary memory unit can store data and information for the process 1801. Memory unit can store data and information that can be used to implement a photothermal therapy, e.g., included in process

1800 and that can be generated from the predictive calculations, algorithms and/or models of the process 1801.

To support various functions of the processing unit, the exemplary I/O unit can be connected to an external interface, source of data storage, or display device. Various types of wired or wireless interfaces compatible with typical data communication standards, such as Universal Serial Bus (USB), IEEE 1394 (FireWire), Bluetooth, IEEE 802.111, Wireless Local Area Network (WLAN), Wireless Personal Area Network (WPAN), Wireless Wide Area Network (WWAN), WiMAX, IEEE 802.16 (Worldwide Interoperability for Microwave Access (WiMAX)), and parallel interfaces, can be used to implement I/O unit. I/O unit can interface with an external interface, source of data storage, or display device to retrieve and transfer data and information that can be processed by the processor, stored in the memory unit, or exhibited on the output unit.

To support various functions of the processing unit, the output unit can be used to exhibit data implemented by the exemplary processing unit. The output unit can include various types of display, speaker, or printing interfaces to implement the exemplary output unit. For example, the output unit can include cathode ray tube (CRT), light emitting diode (LED), or liquid crystal display (LCD) monitor or screen as a visual display to implement the output unit. In other examples, the output unit can include toner, liquid inkjet, solid ink, dye sublimation, inkless (such as thermal or UV) printing apparatuses to implement the output unit; the output unit can include various types of audio signal transducer apparatuses to implement the output unit. The output unit can exhibit data and information, such as patient diagnostic and treatment data, laser irradiation, imaging, and/or computer system machine information, partially processed data processing information, and completely processed data processing information, among other types and forms of data and information. The output unit can store data and information used to implement a photothermal therapy process and from an implemented photothermal therapy process, e.g., such as the process 1800.

In another aspect, a hand-held medical treatment device is disclosed for eliminating cancerous cells in the body, e.g., which can be used to perform photothermal treatment of malignant tumors.

In one exemplary embodiment, the hand-held medical treatment device to administer photothermal therapy to target cells and tissue in the body includes surgical cameras (e.g., fiber optical cameras or imaging devices) that enter into the body via an insertion component and obtain two-and/or three-dimensional images, e.g., which can be used to obtain size, density, and make other necessary calculations. The exemplary device can include one or more other fibers with special 'end' characteristics that are inserted in the body. For example, the end of such fiber(s) can include a coherent light source (e.g., a laser) to be used by a user (e.g., a surgeon) to provide light energy directly at the target. The light energy can be used to provide thermal injury to surrounding cancer cells/malignant tumors, for example, but only has a short radius of execution (e.g., depth of penetration).

For example, the photothermal treatment instrument can be implemented to only kill cells (e.g., provide thermal injury) within dimensions specified with the optical camera, e.g., as opposed to chemotherapy and radiation therapies that provide little to no precision. For example, chemotherapy and radiation can be devastating to the patients overall lifestyle and health (e.g., particularly relevant for children and the elderly). The disclosed photothermal therapy treatment instrument can provide a localized treatment designed particularly for tumors and large masses of cancer, including primary tumors that have not yet metastasized.

The exemplary photothermal treatment device can include another camera or other imaging modality device to see the physical and microscopic (cancer versus non-cancerous) aspects of a tumor. For example, this can determine if there are any cancerous cells and how much of the cancerous cells are remaining after treatment Implementation of the device in such a manner is much more effective than scraping techniques.

In some implementations, the device can be used to change the light source to produce a more 'destructive' optical energy, e.g., such as NIR light combined with the administered gold nanorods. For example, a macromizer can be used to see where to align the instrument to target the region having the cancer cells and provide thermal injury to the malignant tumor. In some instances, some cells around the targeted tumor may be injured, but this would be far less devastating to the body than chemotherapy, intraoperative surgery, and radiation therapy. In some embodiments of the device, the device could be used to administer chemicals or radiation, e.g., coupled into the optical fiber and focused to a narrow beam to target the cancerous area.

The device can include an adjustable insertion component having a reflective backing, in which the adjustable insertion component can be inserted at controlled depths into the body and provide a source to control the penetration depth of the laser beam from the light source. In some examples, the adjustable insertion component can include a light stop mechanism including a metallic surface to provide a terminal depth to the laser penetration. In other examples, the adjustable insertion component can include a tube having an orifice to provide direct injection of the disclosed photothermal functionalized (or nonfunctionalized) biocompatible nanorods into the target tissue. For example, incorporating optical fiber for delivery of the laser to tumors that are not subcutaneous can enhance the disclosed direct injection methods, e.g., which can provide greater precision and efficiency of tumor injury for such treatments beyond the 10 cm depth of penetration of near infrared light.

Figure 20:
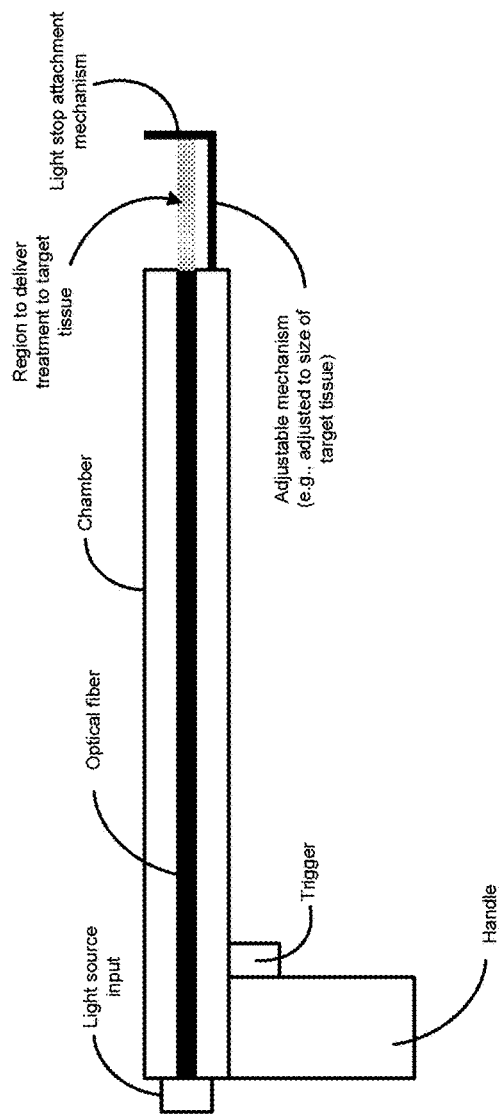
FIG. 20 shows a schematic diagram of an exemplary instrument to administer a photothermal therapy treatment.

FIG. 20 shows a schematic diagram of an exemplary instrument to administer a photothermal therapy treatment. The instrument includes a casing structure including a chamber component coupled to a handle component. The chamber includes an interior that provides a passageway of one or more optical fibers to provide light, e.g., coherent light from a laser at particular wavelengths (e.g., which can be in the near infrared spectral range) from via a light source input of the instrument. In some implementations, the instrument can include an adapter device to assist the coupling of the laser light into the optical fiber(s). The instrument includes the adjustable insertion component, which can include a hose-like/flexible nozzle with optical fiber inside to enable light delivery to non-superficial target tissue. The handle of the casing structure includes a trigger component (e.g., which can be configured as a dial) to control initiation, duration, and conclusion of the photothermal treatment, as well as control output power and intensity of the laser. For example, in some implementations, the trigger component can be used to provide pulses, polarization, etc. The adjustable insertion component can be adjusted to the size of tumor. In the example of the instrument including the light stop mechanism, the metallic surface can be deployed on the other side of the space tending to the size of the tumor. In the example of the photothermal nanorods, the nanostructures can be directly injected into the tumor using the adjustable insertion component to extend a controlled depth where the targeted tissue is located. In some implementations, the device further can include an aspirator, e.g., to remove substances away from the targeted region.

Implementations of the subject matter and the functional operations described in this specification, such as various modules, can be implemented in digital electronic circuitry, or in computer software, firmware, or hardware, including the structures disclosed in this specification and their structural equivalents, or in combinations of one or more of them Implementations of the subject matter described in this specification can be implemented as one or more computer program products, i.e., one or more modules of computer program instructions encoded on a tangible and non-transitory computer readable medium for execution by, or to control the operation of, data processing apparatus. The computer readable medium can be a machine-readable storage device, a machine-readable storage substrate, a memory device, a composition of matter affecting a machine-readable propagated signal, or a combination of one or more of them. The term "data processing apparatus" encompasses all apparatus, devices, and machines for processing data, including by way of example a programmable processor, a computer, or multiple processors or computers. The apparatus can include, in addition to hardware, code that creates an execution environment for the computer program in question, e.g., code that constitutes processor firmware, a protocol stack, a database management system, an operating system, or a combination of one or more of them.

A computer program (also known as a program, software, software application, script, or code) can be written in any form of programming language, including compiled or interpreted languages, and it can be deployed in any form, including as a stand alone program or as a module, component, subroutine, or other unit suitable for use in a computing environment. A computer program does not necessarily correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

The processes and logic flows described in this specification can be performed by one or more programmable processors executing one or more computer programs to perform functions by operating on input data and generating output. The processes and logic flows can also be performed by, and apparatus can also be implemented as, special purpose logic circuitry, e.g., an FPGA (field programmable gate array) or an ASIC (application specific integrated circuit).

Processors suitable for the execution of a computer program include, by way of example, both general and special purpose microprocessors, and any one or more processors of any kind of digital computer. Generally, a processor will receive instructions and data from a read only memory or a random access memory or both. The essential elements of a computer are a processor for performing instructions and one or more memory devices for storing instructions and data. Generally, a computer will also include, or be operatively coupled to receive data from or transfer data to, or both, one or more mass storage devices for storing data, e.g., magnetic, magneto optical disks, or optical disks. However, a computer need not have such devices. Computer readable media suitable for storing computer program instructions and data include all forms of non volatile memory, media and memory devices, including by way of example semiconductor memory devices, e.g., EPROM, EEPROM, and flash memory devices. The processor and the memory can be supplemented by, or incorporated in, special purpose logic circuitry.

While this patent document contains many specifics, these should not be construed as limitations on the scope of any invention or of what may be claimed, but rather as descriptions of features that may be specific to particular embodiments of particular inventions. Certain features that are described in this patent document in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. Moreover, the separation of various system components in the embodiments described above should not be understood as requiring such separation in all embodiments.

Only a few implementations and examples are described and other implementations, enhancements and variations can be made based on what is described and illustrated in this patent document.

What is claimed is:

1. A hand-held device to administer a photothermal treatment, comprising:
    a housing including a chamber component coupled to a handle component, the chamber including a hollowed interior;
    a light source input to receive coherent light at particular wavelengths from a light source;
    one or more optical fibers configured in the hollowed interior and coupled to the light source input;
    an adjustable insertion component configured in the chamber and capable of penetrating into tissue of a body to a distance, the adjustable insertion component including a passageway to extend the one or more optical fibers to the distance;
    a trigger to enable or disable the transmittance of the coherent light from the device to a target tissue, and
    a fluidic channel configured in at least a portion of the chamber and through the adjustable insertion component to deliver photothermal nanostructures directly to the target tissue.

2. The device of claim 1, further comprising an adapter to optically couple the light source generating the coherent light with the one or more optical fibers.

3. The device of claim 1, further comprising an aspirator to remove substances away from the target tissue.

4. The device of claim 1, wherein the particular wavelengths include near infrared wavelengths.

5. The device of claim 1, wherein said trigger is configured as a dial to also control output power and intensity of the device.

6. The device of claim 1, further comprising a light stop attachment mechanism.

\* \* \* \* \*